United States Patent [19]
Koestner et al.

[11] Patent Number: 5,139,020
[45] Date of Patent: Aug. 18, 1992

[54] METHOD AND APPARATUS FOR CONTROLLING THE HEMODYNAMIC STATE OF A PATIENT BASED ON SYSTOLIC TIME INTERVAL MEASUREMENTS DETECTING USING DOPPLER ULTRASOUND TECHNIQUES

[75] Inventors: Ken Koestner; Tibor A. Nappholz, both of Englewood; Harry L. Valenta, Jr., Aurora; Steven M. Maas, Englewood, all of Colo.

[73] Assignee: Telectronics Pacing Systems, Inc., Englewood, Colo.

[21] Appl. No.: 667,305

[22] Filed: Mar. 8, 1991

[51] Int. Cl.$^5$ .......................... A61B 8/12; A61N 1/36
[52] U.S. Cl. .......................... 128/419 PG; 128/661.1; 128/662.04; 128/662.06
[58] Field of Search ..................... 128/660.03, 662.04, 128/662.06, 661.1, 713, 419 P, 419 PG

[56] References Cited

U.S. PATENT DOCUMENTS

| | | | |
|---|---|---|---|
| 3,951,140 | 4/1976 | Eggleton et al. | 128/660.03 |
| 4,319,580 | 3/1982 | Colley et al. | 128/661 |
| 4,429,697 | 2/1984 | Nappholz et al. | 128/419 PG |
| 4,527,568 | 7/1985 | Rickards | 128/419 PG |
| 4,541,433 | 9/1985 | Baudino | 128/662.06 X |
| 4,637,401 | 1/1987 | Johnston | 128/662.06 |
| 4,686,987 | 8/1987 | Salo et al. | 128/419 PG |
| 4,708,143 | 11/1987 | Schroeppel | 128/419 PG |
| 4,719,921 | 1/1988 | Chirife | 128/419 PG |
| 4,766,900 | 8/1988 | Callaghan | 128/419 PG |
| 4,773,401 | 9/1988 | Citak et al. | 128/419 PG |
| 4,821,724 | 4/1989 | Whigham et al. | 128/419 P |
| 4,841,981 | 6/1989 | Tanabe et al. | 128/713 X |
| 4,901,725 | 2/1990 | Nappholz et al. | 128/419 PG |
| 4,967,753 | 11/1990 | Haase et al. | 128/662.06 |
| 5,027,816 | 7/1991 | Cohen | 128/419 PG |

OTHER PUBLICATIONS

J. L. Wessale et al., "Cardiac Output Versus Pacing Rate at Rest and With Exercise in Dogs With AV Block," PACE, vol. 11, pp. 575-582 (May 1988).

*Primary Examiner*—Francis Jaworski
*Attorney, Agent, or Firm*—Gottlieb, Rackman & Reisman

[57] ABSTRACT

A hemodynamic control apparatus and method for regulating blood flow within the cardiovascular system in a closed-loop control system using ultrasound measurement techniques and intracardiac electrogram sensing to determine a hemodynamic status of the patient and to derive a control parameter for modulating the hemodynamics of the system using electrical or pharmaceutical therapy. This apparatus and method provides for the monitoring of heart contractility and blood flow volume in the circulatory system to control an implantable cardiac assist or therapy device to maintain the hemodynamic status of the patient without invading the left heart or the arterial system of the patient.

19 Claims, 9 Drawing Sheets

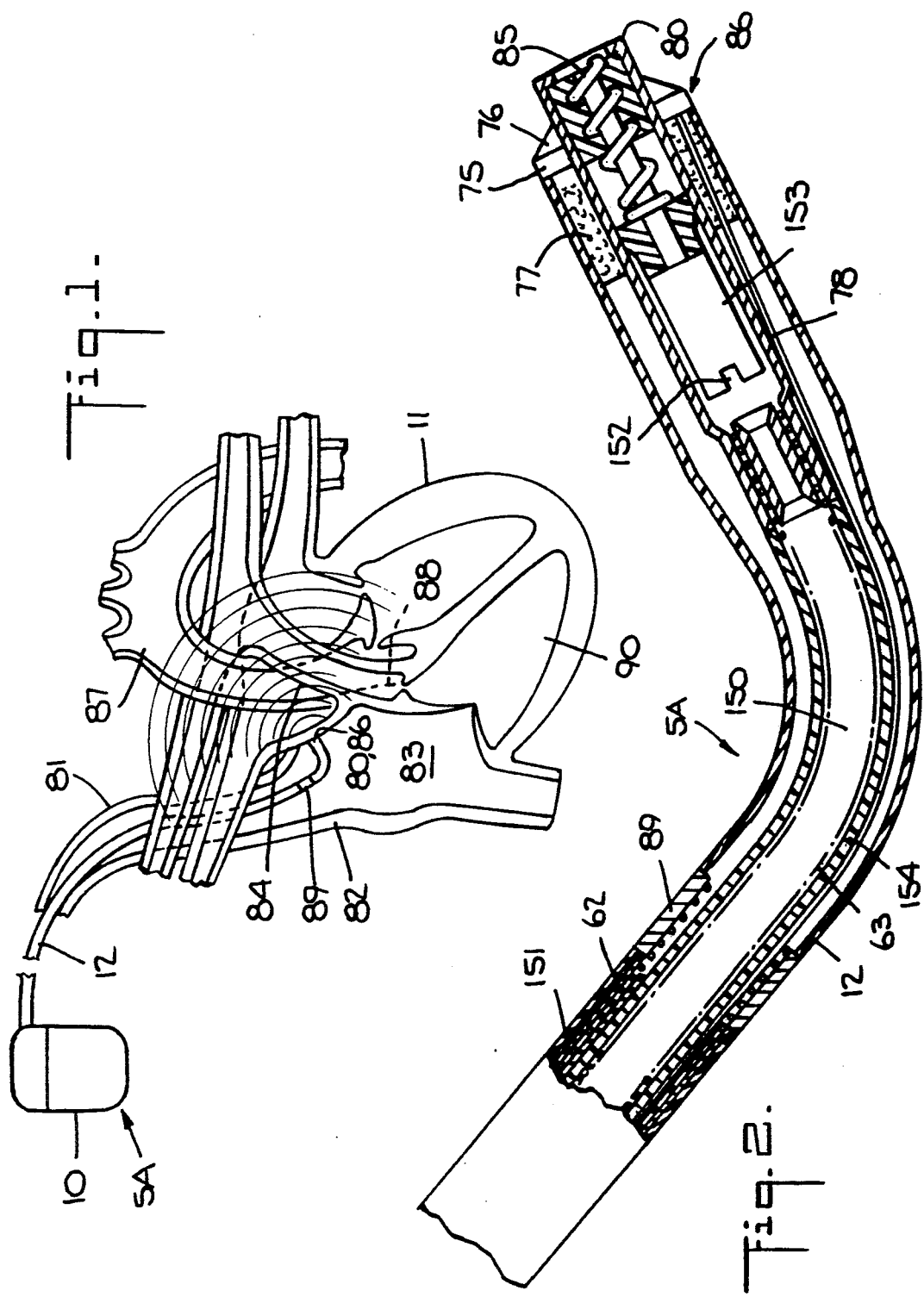

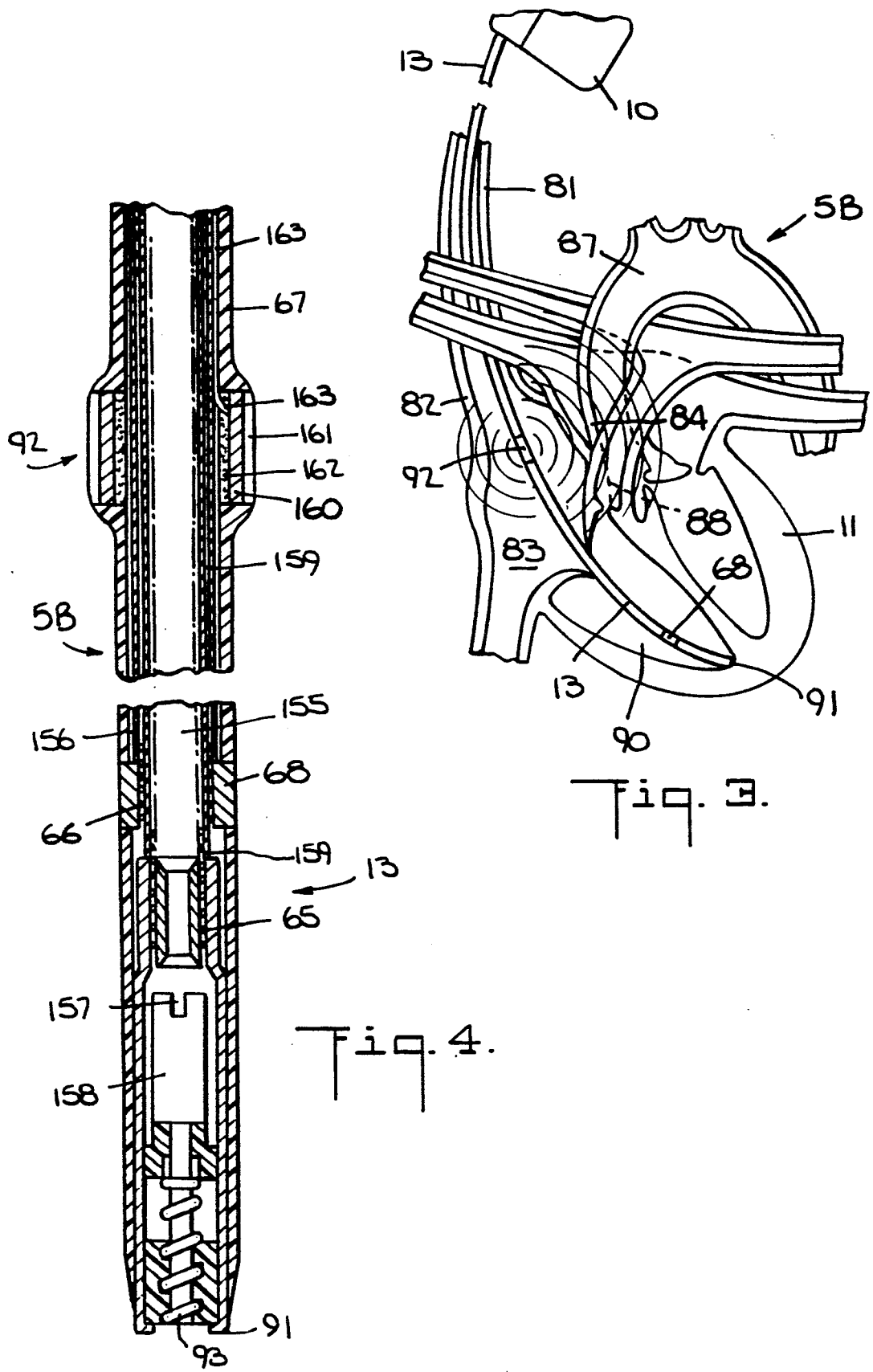

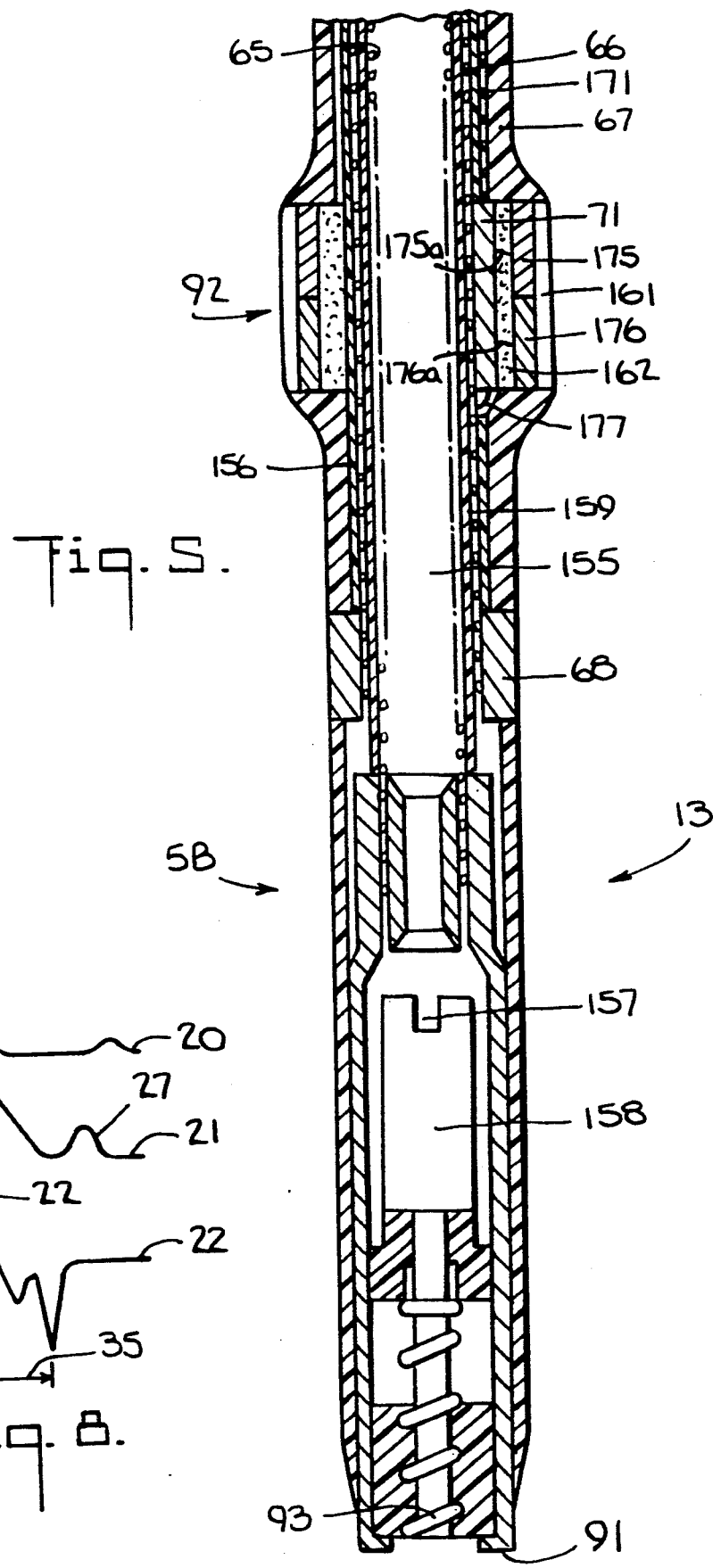

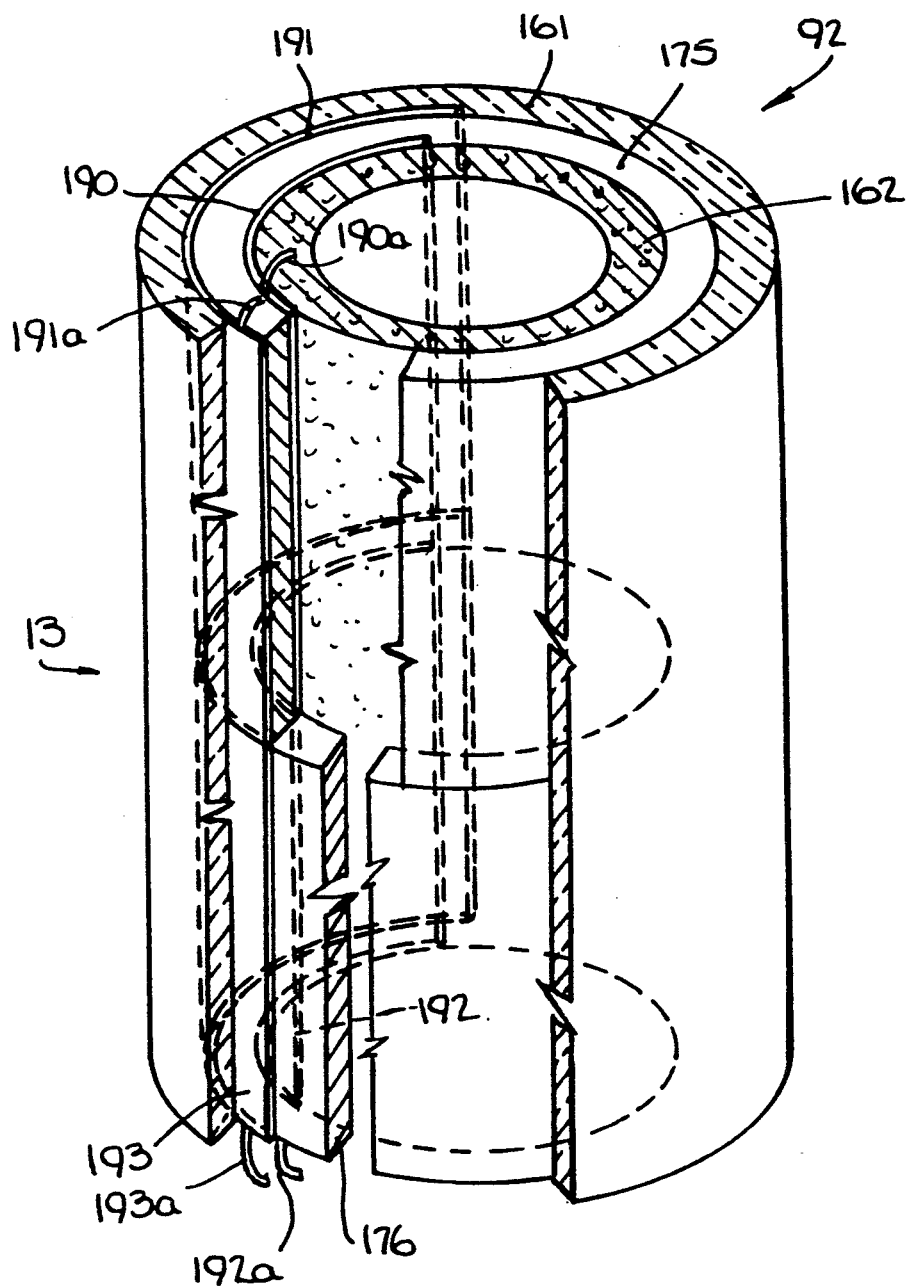

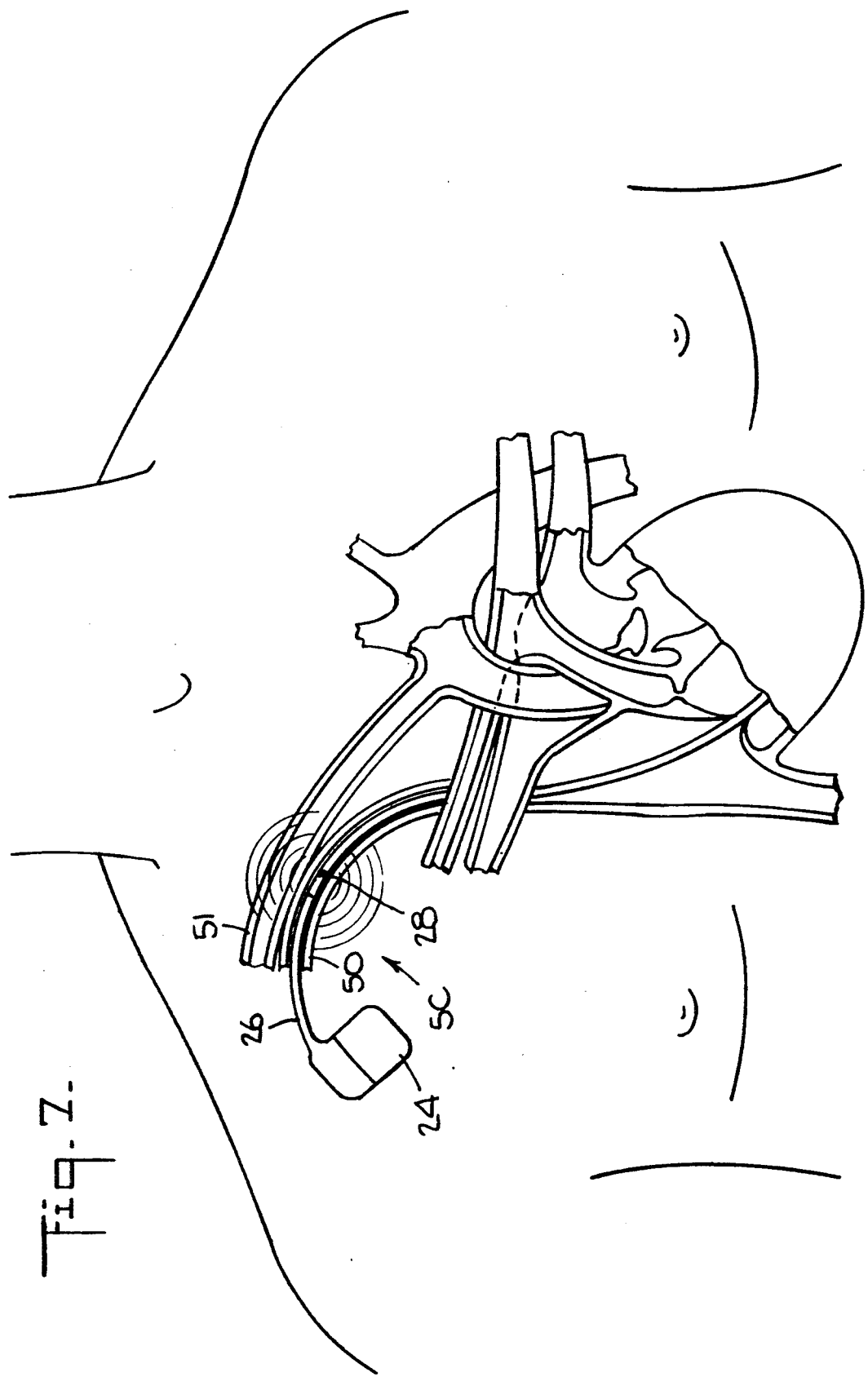

METHOD AND APPARATUS FOR CONTROLLING THE HEMODYNAMIC STATE OF A PATIENT BASED ON SYSTOLIC TIME INTERVAL MEASUREMENTS DETECTING USING DOPPLER ULTRASOUND TECHNIQUES

TECHNICAL FIELD

This invention generally relates to an implantable cardiac assist device and, more particularly, to an apparatus and method for performing cardiac hemodynamic monitoring and therapeutic control operations by measuring systolic time intervals, which are detected using Doppler ultrasound measurement techniques, and by applying a therapy based on the results of this measurement.

BACKGROUND OF THE INVENTION

Any device intended to control hemodynamics of the circulatory system in patients with cardiac injury or disease requires a mechanism for efficiently assessing the patient's hemodynamic status. The performance of the heart's left ventricle is a primary determinant of hemodynamic status. The measurement of blood pressure within the left ventricle would accurately provide a parameter directly related to left ventricular function. However, there is no practical means for measuring pressure within the left ventricle. The measurement of blood pressure within the peripheral systemic circulatory system provides some assessment of left ventricular performance. Unfortunately, these measurements are inaccurate due to the variability in blood pressure resulting from peripheral influences such as differences in the contractility of peripheral blood vessels. More accurate information regarding left ventricular function is provided by combining blood pressure measurements from the peripheral circulatory system with those from either of the right chambers of the heart.

The heart may be more accurately modelled as a constant volume pump than as a constant pressure pump. Therefore, a better criterion for assessing the hemodynamic status of the circulatory system is provided by measurements of the volume of blood flow pumped from the heart, rather than blood pressure determinations. In a constant volume system, the parameters of end diastolic volume, ventricular filling, cardiac output, and the contractility of the heart muscle accurately describe the pumping performance of the heart. Each of these parameters is directly related to cardiac contractility. A systolic time interval is a characteristic measurement of a time interval separating one or more electrical and mechanical cardiac events. The measurement of appropriate systolic time intervals, in combination with an analysis of timed blood flow volumes, allows the accurate estimation of some of the aforementioned hemodynamic parameters.

The contractility of the heart muscle determines the forces and pressures generated within the heart. As the heart muscle contracts, the pressure increases in the heart chamber. In turn, the changes in pressure control the opening and closing of heart valves and thereby regulate the blood flow from one chamber into another and from the left ventricle into the systemic and pulmonary circulatory systems. The timing of these electrical and mechanical events reflects the pressures generated within the heart. Cardiac contractility and intraventricular pressures and forces are difficult to measure. In contrast, the relative timing of heart valve opening and closing events and the correlation of these mechanical events with cardiac electrical polarization events is a measurable quantity which is expressed as a systolic time interval parameter. By determining cardiac contractility in this manner, an apparatus can assess whether the cardiovascular system is adequately supporting the needs of the body. Myocardial contractility, as derived in the form of systolic time intervals, is appropriate for usage as a control parameter in a closed-loop hemodynamic control system. Some measurements, which are known in the prior art, are less directly related to the hemodynamic functionality of the heart.

The fundamental advantage of a hemodynamic control method based on the measurement of cardiac contractility or its direct corollary, cardiac output, and its usage to control a cardiac assist device is illustrated by the three-phase relationship between cardiac output and pacing rate shown in a report by J. L. Wessale et al., entitled "Cardiac Output Versus Pacing Rate At Rest And With Exercise In Dogs With AV Block", *PACE*, Vol.11, page 575 (1988). At low pacing rates (first phase), the cardiac output increases proportional to pacing rate. At some point (second phase), further increases in pacing rate cause the cardiac output to rise only slightly, if at all. At still higher pacing rates (third phase), further increases will cause the cardiac output to diminish. The width of the second phase is considered an indication of the pumping capacity of the ventricles and the health of the heart. Rate-responsive pacemakers cannot determine the phase of the cardiac output/pacing rate relationship for a given pacing rate without measuring cardiac output.

Some prior art devices measure physiological and physical parameters other than cardiac contractility, and regulate hemodynamics accordingly. Hemodynamic control in such devices is performed in an open-loop, rather than a closed-loop, manner since the relationship between the actual hemodynamic state, as defined by the cardiac contractility, and the measured control parameter is not known. The response of such devices is less directly related to the response of the heart since the hemodynamic status is characterized by a parameter related only secondarily to such status. The prior art includes a number of pacemakers, called rate-responsive pacemakers, each of which adjusts the heart rate of a patient based on a measurement acquired using a sensor to derive a parameter related in some manner to metabolic demand. Cardiac electrical activity (either stimulated or natural), body motion, respiration and temperature are examples of such parameters for assessing metabolic demand in a cardiac control device.

The method of determining metabolic demand using each of these measured parameters requires the previous correlation of the parameter with cardiac output by means of clinical experimentation. These correlation relationships are subject to wide variability from patient to patient and from one test to the next in an individual patient. More importantly, each of the parameters is subject to influences from physiological and physical sources which are unrelated to cardiac output and metabolic demand. The influences affecting these measurements are poorly understood and difficult to characterize. Furthermore, since the secondarily-related metabolic indicator pacing rates do not take the actual output from the heart into account, they may actually hinder the ability of the heart to meet the necessary metabolic demand, as illustrated in the aforementioned report by Wessale. As a consequence, all sensing and control means using a control parameter which is secondarily related to cardiac output and metabolic demand suffer from the inability to assess the hemodynamic status of the cardiovascular system.

Dual chamber heart pacers have been developed in order to generate sequential atrial and ventricular pacing pulses which closely match the physiological requirements of a patient. A conventional dual chamber heart pacer, as disclosed in U.S. Pat. No. 4,429,697 to Nappholz et al., dated Feb. 7, 1984, and entitled "Dual Chamber Heart Pacer with Improved Ventricular Rate Control," includes atrial and ventricular beat sensing and pulse generating circuits. It is known that the detection of a ventricular beat or the generation of a ventricular pacing pulse initiates the timing of an interval known as the V-A delay. If an atrial beat is not sensed prior to expiration of the V-A delay interval, then an atrial pacing pulse is generated. Following the generation of an atrial pacing pulse, or a sensed atrial beat, an interval known as the A-V delay is timed. If a ventricular beat is not sensed prior to the expiration of the A-V delay interval, then a ventricular pacing pulse is generated. With the generation of a ventricular pacing pulse, or the sensing of a ventricular beat, the V-A delay timing starts again. This patent describes how the V-A delay timing interval may be divided into three parts; the atrial refractory period, the Wenkeback timing window, and the P-wave synchrony timing window. It outlines the importance of controlling rate in order to maintain synchrony between the atrium and the ventricle. The patent does not, however, address the issue of sensing the metabolic demand of the patient and distinguishing between high atrial rates due to pathological tachycardia and high atrial rates expected when the patient exercises. The dual chamber pacer, under the influence of atrial control, may correctly set a high heart rate when it senses heightened electrical activity resulting from normal physical exertion. When the same sensing system detects a heightened electrical activity arising from a pathological tachycardia episode, having similar electrical frequency and amplitude characteristics, it will incorrectly elevate the heart rate, endangering the health of the patient.

In other examples, it is known in the prior art to electrically sense and measure natural or evoked (stimulated) cardiac potentials and analyze these signals to derive parameters such as Q-T intervals or evoked potential depolarization gradients. These are disclosed, respectively, in Rickard's U.S. Pat. No. 4,527,568, entitled "Dual Chamber Pacer with Alternative Rate Adaptive Means and Method", issued Jul. 9, 1985, and in Callaghan's U.S. Pat. No. 4,766,900, entitled "Rate Responsive Pacing System using the Integrated Cardiac Event Potential", issued Aug. 30, 1988. The efficacy of this sensing and control method depends largely on the signal amplitude and timing characteristics of the cardiac repolarization waveform, which is erratically influenced by many physiological, pharmacological and electrical phenomena. These phenomena are poorly understood, frequently leading to an unstable control behavior in devices using such sensing and control methods.

It is known in the prior art of cardiac pacemakers to control pacing rate based on the determination of cardiac output. In one example (Salo et al. in U.S. Pat. No. 4,686,987, entitled "Biomedical Method and Apparatus for Controlling the Administration of Therapy to a Patient in Response to Changes in Physiological Demand", issued Aug. 18, 1987), the device estimates cardiac output using intracardiac impedance measurements between two spaced electrodes disposed within the right ventricular cavity. This apparatus measures the blood impedance by injecting subthreshold (nonstimulating) electrical current pulses into the heart through one electrode and detecting the current at the second electrode. From changes in impedance, this device estimates changes in left ventricle volume by integrating the measurements over time, leading to the estimation of cardiac output. Unfortunately, inherent in the usage of impedance as a control parameter is the lack of a reliable relationship between impedance and actual cardiac output sought as the basis for control. When a device measures impedance using only two electrodes, gross volume approximation errors occur which are magnified during the integration process leading to the determination of cardiac output. In addition, since the electrodes are necessarily implanted into the right rather than the left ventricle (the left ventricle is not available for access) and the estimate of left ventricular volume in this manner is very crude and inaccurate, the cardiac output estimate derived using impedance techniques is highly susceptible to cumulative errors in each of the integration steps. Furthermore, extraneous influences on the impedance signal such as noise from respiration, changes in the patient's posture, and electrical interference produce a large noise signal and lead to further errors.

One recent development in cardiac monitoring and control is the implantable pressure sensor. Schroeppel describes one example of such control in U.S. Pat. No. 4,708,143, entitled "Method for Controlling Pacing of a Heart in Response to Changes in Stroke Volume", issued Nov. 24, 1987. Existing cardiac control systems using pressure sensors measure atrial and venous pressures to determine absolute and relative pressure changes during the cardiac cycle, to measure time intervals between electrophysiological phenomena, and to derive an estimate of cardiac output or stroke volume from these measurements. Pressure sensors, even when used in the most effective manner, are implantable only in locations which allow direct measurement of pressure within the right heart, rather than in the left ventricle. Measurements from the right heart poorly estimate the true hemodynamic state of the patient.

It is known in the art for a cardiac pacemaker to measure a systolic time interval for the purpose of using this parameter to control cardiac pacing rate. Such devices sense cardiac electrical events from intracardiac electrograms, sense cardiac mechanical events in various manners, and correlate the timing of these mechanical and electrical events to determine systolic time intervals, including pre-ejection period and left ventricular ejection time. In turn, these devices use the systolic time interval to determine a rate control parameter. None of these prior art devices detect mechanical cardiac events using Doppler ultrasound measurement techniques. In U.S. Pat. No. 4,708,143, discussed previously, a pacemaker uses piezoelectric sensing to measure ejection time. From ejection time, the pacemaker estimates stroke volume and correlates the stroke volume estimate with heart rate.

In U.S. Pat. No. 4,719,921 to Chirife, entitled "Cardiac Pacemaker Adaptive to Physiological Requirements", issued Jan. 19, 1988, a pacemaker uses a blood pressure sensor to detect variations in the blood pressure waveform in the peripheral vascular system or right ventricle. The pacemaker analyzes mechanical cardiac events measured from the blood pressure waveform to determine pre-ejection intervals and set the heart rate from these intervals. Because it is not possible to measure blood pressure in either the arterial system or the left ventricle, this technique of controlling cardiac pacing from the pre-ejection period measurement is subject to large errors which degrade the pacemaker's rate responsive behavior.

In U.S. Pat. No. 4,773,401 to Citak et al., entitled "Physiological Control of Pacemaker Rate using Pre-ejection Interval as the Controlling Parameter", issued Sep. 27, 1988, a pacemaker senses impedance measurements from a multi-electrode lead, positioned within the right ventricle, to measure the time from the QRS-complex of the intracardiac electrogram to the first positive crossing of the impedance signal average. The pacemaker uses this time to estimate pre-ejection period for the purpose of controlling pacing rate. The impedance measurement is susceptible to noise which produces large errors in measured time intervals. Unfortunately, to correctly set the pacing rate, the time interval measurement must be very precise.

Each of the prior art techniques for estimating systolic time intervals and relating such intervals to myocardial contractility are inaccurate and complex. The primary source of inaccuracy is the lack of access to direct measurements within the left ventricle.

It is also known in the art to use noninvasive Doppler ultrasound techniques to measure the maximum blood flow velocity in the aorta or pulmonary artery and to determine cardiac output as a product of the time average mean velocity and the estimated cross-sectional area. One such usage of Doppler ultrasound techniques is described by Colley et al. in U.S. Pat. No. 4,319,580, entitled "Method for Detecting Air Emboli in the Blood in an Intracorporeal Blood Vessel", issued Mar. 16, 1982. Devices use these prior art ultrasound techniques to monitor cardiovascular hemodynamics by measuring cardiac output and stroke volume, but do not use these measurements to control cardiac functions.

SUMMARY OF THE INVENTION

In accordance with one aspect of the present invention, there is provided a cardiac monitoring and therapy device which controls blood flow in a patient's cardiovascular system by accurately measuring at least one systolic time interval using Doppler ultrasound techniques to detect cardiac mechanical events. The invention utilizes a Doppler ultrasound measuring transducer mounted on a catheter which is implanted in one of the right chambers of the heart so that the sonic axis of the ultrasound beam is directed toward the left ventricle or aortic root. In the preferred embodiment of the invention, a miniature ultrasound transducer is implanted in the superior vena cava or high right atrium with its sensing field of view directed towards the ascending aorta. This method of implantation enables highly accurate detection of changes in the relative amount of blood flowing from the left ventricle of the heart. Another implementation of the present invention involves the measurement of systolic time intervals by ultrasonically interrogating the right or left subclavian artery from an ultrasonic sensor implanted in one of the right chambers of the heart to directly measure blood pulse wave velocity without invading the left heart or arterial system. A further embodiment of the present invention entails the implantation of an ultrasound transducer in a vein to irradiate a nearby artery for the purpose of determining peripheral blood flow velocity in such a proximal artery. In this manner, the device measures pulse wave velocity in the arterial system, which is not accessible for measurement, using at least one catheter-mounted sensor which is implanted within a vein and thereby accessible using procedures which are standard in the art of electrophysiology.

The device measures systolic time intervals by detecting or generating cardiac electrical events and determining the time intervals between these electrical events and mechanical events defined within the structure of the Doppler ultrasound waveform. These intervals signify the timing of mechanical events within the cardiac cycle and indicate the pressures and forces generated by the myocardial contractile elements. The device derives a hemodynamic control parameter based on the gradual relative changes in the systolic time intervals and uses this parameter to chronically monitor and control the hemodynamic status of the patient. Preferably, the device controls blood flow by applying electrical stimulation pulses to the heart, or by administering pharmaceutical agents by controlling the output of an implantable drug infusion pump.

When using Doppler ultrasound measurement techniques in connection with hemodynamic monitoring and cardiac therapeutic control operations, the transducer radiates cardiovascular tissue with acoustic energy transmitted at ultrasonic frequencies. The device processes returning echoes to extract the audio portion of Doppler ultrasound signals by measuring the shift in frequency of the returning echoes in comparison to the transmitted waves. Next, the device analyzes the signals to measure and temporarily store these signals which relate to the quantity of blood flowing within the circulatory system per unit of time. These records form a blood flow velocity time waveform representing the maximum instantaneous flow velocity of blood cells within the ultrasonic field. The device measures the volume blood flow waveform, differentiates the waveform values with respect to time, and detects peaks in the derivative waveform. These peaks are defined as event markers which delineate the timing of mechanical events within the cardiac cycle. During the time intervals when the apparatus is measuring blood flow, it also detects cardiac electrical potentials, and correlates the time waveform of the blood flow measurements with the timing of cardiac electrical events to quantify the hemodynamic status as a parameter called systolic time intervals. These intervals are correlated with myocardial contractility. Once this characteristic measurement of hemodynamic status is quantified, the apparatus uses it to control a medical therapy in a closed-loop feedback control system. The preferred embodiment of the invention performs a number of redundant determinations of cardiac contractility by measuring the Doppler waveform slope, the maximum rate of change in blood flow velocity in the aorta in response to a heart beat. This slope measurement is a known reliable indication of cardiac contractility.

The apparatus and method disclosed is useful in cardiac pacemakers, tachycardia reversion devices, defibrillators, drug infusion pumps and other implantable cardiac assist devices. The present invention differs from previous devices by using Doppler ultrasound techniques to derive a closed-loop control parameter based on at least one systolic time interval to control a hemodynamic therapy. The closed-loop control parameter allows the device to control electrical stimulation therapy, either cardiac pacing or cardioversion and defibrillation, by varying one or more of the stimulation timing, frequency, amplitude, duration, pulse morphology and pattern. A cardiac pacemaker may use the measured blood flow parameter to control pace delivery timing, pacing rate, pacing mode, and parameters defining the stimulating pulse including stimulus amplitude, duration, phase and morphology. The parameter also can control an implantable drug infusion pump by varying the timing and dosage of a pharmaceutical substance in drug therapy.

The preferred embodiment of the present invention is a hemodynamic control apparatus operating as a cardiac pacemaker which may function in either a dual-chamber mode (DDDR) or a single-chamber mode (VVIR). In a DDDR mode, the atrium and ventricle operate in synchrony. At high atrial rates, this synchronous behavior may be inappropriate or harmful. The pacemaker detects when synchronous behavior is harmful by estimating myocardial contractility from systolic time interval measurements. The pacemaker determines when ventricular activity should not occur following a natural atrial heart beat and changes the pacing mode to VVIR mode, accordingly. From this indication of myocardial contractility, the pacemaker can determine whether the heart successfully responds to a pacing stimulus of a particular amplitude and pulse duration, for the purpose of safely adjusting these pacing parameters to minimize energy expenditure and discomfort to the patient while maintaining hemodynamic sufficiency.

Further objects, features and advantages of our invention will become apparent upon consideration of the following detailed description in conjunction with the accompanying drawings.

BRIEF DESCRIPTION OF THE DRAWINGS

FIG. 1 is a fragmentary perspective view, with parts cut away for clarity, of one embodiment of the invention, illustrating a pacemaker, a catheter or lead and a Doppler ultrasound sensor shown within the anatomical context of a cardiovascular environment in which the system is implanted;

FIG. 2 is an enlarged fragmentary view, with parts cutaway for clarity, of the lead shown in FIG. 1;

FIG. 3 is a fragmentary perspective view, with parts cut away for clarity, of a second embodiment of the invention, illustrating the pacemaker, the lead and the Doppler ultrasound sensor shown within the anatomical context of a cardiovascular environment in which the system is implanted;

FIG. 4 is an enlarged fragmentary view, with parts cutaway for clarity, of the lead shown in FIG. 3;

FIG. 5 is an enlarged fragmentary view, similar to FIG. 4, of another embodiment of the lead shown in FIG. 3;

FIG. 6 is a partial perspective view of the Doppler ultrasound crystal carried by the leads shown in FIG. 5;

FIG. 7 is a fragmentary perspective view of a third embodiment of the invention, illustrating a chronically implantable peripheral vascular monitor, including a lead and the Doppler ultrasound sensor shown within the anatomical context of a peripheral vascular environment in which the system is implanted;

FIG. 8 comprises a series of graphical representations along a time axis of an intracardiac electrogram, a Doppler waveform and a differentiated Doppler signal, showing a correspondence in timing between the various signals;

DETAILED DESCRIPTION

Figure 9:
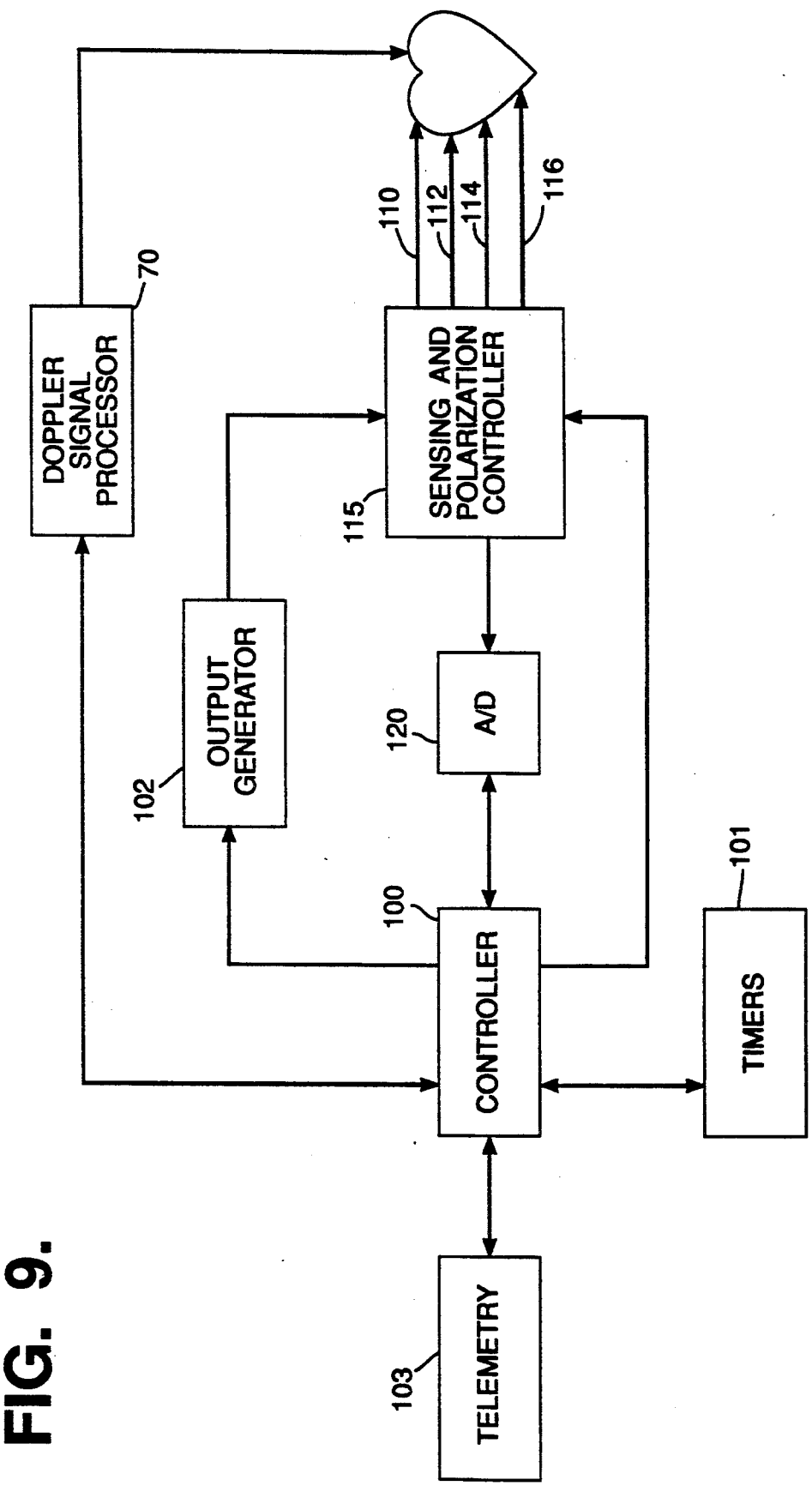
FIG. 9 is a high-level schematic block diagram of an illustrative embodiment of the invention.

FIGS. 1 and 2 illustrate a first example of a cardiac assist or therapy device, shown generally at 5A, in the form of a cardiac pacemaker 10 having an atrial cardiac catheter or lead 12 connecting the pacemaker 10, physically and electrically, to an atrial pacing tip electrode 80. The atrial cardiac lead 12 extends from pacemaker 10 through a patient's cardiovascular system from a vein 81 leading to the superior vena cava 82, through the right atrium 83 and extending into the high right atrium or the atrial appendage 84 of the heart 11, where the atrial pacing tip electrode 80 is implanted. It is known in the art that ultrasonic Doppler probes are capable of long-term viability in an implanted environment.

The atrial pacing tip electrode 80 is implanted into the high right atrium or atrial appendage 84 using an active fixation mechanism such as an atrial lead helical spring 85 (shown in FIG. 2). An annular piezoelectric ultrasound transducer 86 is affixed to the atrial cardiac lead 12 adjacent to the atrial pacing tip electrode 80. Implantation of the atrial pacing tip electrode 80 is performed in a manner such that the ultrasound beam axis of the crystal ultrasound transducer 86 is directed towards and into the ascending aorta 87, allowing the measurement of blood flowing in the ascending aorta 87. Alternatively, the beam axis may be directed toward and into the subclavian artery for measurement of blood flow in that vessel. Implantation of the catheters and sensors in this manner requires the usage of only conventional catheter-based right heart techniques. In the former case, the device 5A derives a measurement of cardiac output at the aortic root 88. The ability to measure the cardiac output at the aortic root using Doppler ultrasound is important because it enables the implementation of a fully closed-loop cardiac system for monitoring and controlling blood flow. Automatic control of metabolic demand and hemodynamic status is possible only if cardiac output at the aortic root is known.

FIG. 2 shows the atrial cardiac lead portion 12 of device 5A in greater detail and illustrates the arrangement of annular piezoelectric ultrasound transducer 86 relative to the lead 12, an atrial pacing ring electrode 89, atrial pacing tip electrode 80 and atrial lead helical spring 85. An active fixation device such as atrial lead helical spring 85, is normally affixed to atrial tissue when an appropriate activating member or stylet (not shown), which may be passed through lumen 150 of catheter 12, engages a slot 152 in a rotationally supported driving member 153, and is rotated, as is well known in the art. Two wire coil conductors 62 and 63, which are separated by an intermediate insulating tube 154, extend longitudinally within an outer insulating tube 151 to connect atrial pacing ring electrode 89 and atrial pacing tip electrode 80, respectively, with a suitable connector (not shown) to pacemaker 10. The annular piezoelectric ultrasound transducer 86 transmits and receives through an epoxy window 76, ultrasonic energy, generated by means of an annular ultrasound crystal 75, which is affixed to an epoxy base containing hollow glass spheres 77. Epoxy window 76 may be composed of polyethelene or parazylene. Hollow glass spheres 77 provide a dampening effect on the received ultrasound energy. Ultrasound crystal 75 is electrically connected with ultrasound signal processing circuitry (not shown in this figure) within pacemaker 10 by means of a micro-coaxial cable 78.

FIGS. 3 and 4 illustrate a second example of a cardiac assist or therapy device, shown generally at 5B, in the form of a pacemaker 10 having a ventricular cardiac catheter or lead 13 connecting the pacemaker 10, physically and electrically, to a ventricular pacing tip electrode 91. The ventricular cardiac lead 13 extends from pacemaker 10 through a patient's cardiovascular system from a vein 81 leading to the superior vena cava 82, through the right atrium 83 and then into the right ventricle 90 of the heart 11, where the ventricular pacing tip electrode 91 is implanted.

The ventricular pacing tip electrode 91 is implanted into the apex of the right ventricle 90 using standard electrophysiology techniques in which an active fixation mechanism such as a ventricular lead helical spring 93 (shown in FIG. 4) affixes the electrode to the cardiac tissue. At an appropriate location on the ventricular cardiac lead 13, a cylindrical piezoelectric ultrasound transducer 92, having the form of a tube or ring, encircles and joins electrically with the ventricular cardiac lead 13. Implantation of the ventricular pacing tip electrode 91 is performed in a manner such that the cylindrical piezoelectric transducer 92 is situated within the superior vena cava 82 or high in the right atrium 83. Pacemaker 10 electrically excites the ultrasound transducer 92, causing the piezoelectric elements of the transducer to emit ultrasound waves which extend in all directions perpendicular to the surface of the cylindrical transducer 92. The emitted ultrasonic waves interrogate the blood and tissue in nearly a spherical pattern. Since the ascending aorta 87 characteristically has the largest blood volume and highest blood flow velocity within the detection range of the transducer, the ultrasound signals having the greatest amplitude returning to the transducer 92 predominantly reflect the influence of blood flow within the ascending aorta. Signals returning from other blood vessels are attenuated by intervening tissue and have a much lower amplitude. Pacemaker 10 control circuitry classifies these extraneous signals as background noise.

FIG. 4 shows the ventricular cardiac lead portion 13 of device 5B in greater detail and illustrates the arrangement of cylindrical piezoelectric ultrasound transducer 92, a ventricular pacing ring electrode 68, the pacing tip electrode 91, and the ventricular lead helical spring 93. An active fixation device, such as the ventricular lead helical spring 93, is normally affixed to ventricular tissue when an appropriate activating member or stylet (not shown) disposed in lumen 155 of catheter 13 engages a slot 157 in a rotationally supported driving member 158, and is rotated. Two wire coil conductors 66 and 65, which are separated by an intermediate insulating tube 159, extend longitudinally within an outer insulating tube 156 to connect ventricular pacing ring electrode 68 and ventricular pacing tip electrode 80, respectively, with a suitable connector (not shown) to pacemaker 10. The cylindrical piezoelectric ultrasound transducer 92 includes a cylindrical crystal 160, positioned between an epoxy window 161 on the exterior and an epoxy substrate 162 in the interior. The epoxy substrate 162 is filled with hollow glass spheres to dampen the received ultrasonic energy. The cylindrical crystal 160 is electrically connected with ultrasound signal processing circuitry (not shown in this figure) within the pacemaker 10 by means of a micro-coaxial cable 163 which is interposed between outer insulating tube 156 that surrounds coil 66 and an exterior silastic sheath 67. When ventricular pacing tip electrode 91 is implanted in the apex of the right ventricle 90 of FIG. 3, the length of the portion of the lead extending from the pacing tip electrode 91 to the cylindrical piezoelectric ultrasound transducer 92 is selected to place the transducer either within the superior vena cava 82 or high in the right atrium 83 of FIG. 3, according to the desires of the surgeon. In this manner, a surgeon implants the catheters and sensors using conventional catheter-based right heart techniques.

FIG. 5 shows an additional embodiment of the ventricular cardiac lead portion 13 of device 5B which was previously illustrated in FIG. 4. The FIG. 5 embodiment includes a probe IC or miniature integrated circuit 71, which performs high frequency signal processing of ultrasound signals. FIG. 5 illustrates the arrangement of cylindrical piezoelectric ultrasound transducer 92, the ventricular pacing ring electrode 68, the ventricular pacing tip electrode 91, and the ventricular lead helical spring 93. As before, the ventricular lead helical spring 93 is affixed to ventricular tissue by an appropriate activating member or stylet (not shown) that is passed through lumen 155 into engagement with the slot 157 in rotationally supported driving member 158, and rotated. Two wire coil conductors 66 and 65, which are separated by an intermediate insulating tube 159, extend longitudinally within outer insulating tube 156 to connect ventricular pacing ring electrode 68 and ventricular pacing tip electrode 91, respectively, with a suitable connector (not shown) to pacemaker 10. The cylindrical piezoelectric ultrasound transducer 92 includes cylindrical ultrasound transmission and receiving crystals 175 and 176, respectively, positioned between epoxy window 161 on the exterior and epoxy substrate 162 in the interior. The epoxy substrate 162 is filled with hollow glass spheres to dampen the received ultrasonic energy.

The probe IC 71 is electrically interconnected with cylindrical ultrasound transmission crystal 175 and cylindrical ultrasound receiving crystal 176 by respective pairs of conductors represented diagrammatically at 175a and 176a. It is mounted on the outer coil 66 within the ultrasound transducer 92. Probe IC 71 processes the high frequency ultrasound signals into low frequency data, obviating the need for the micro-coaxial cable 163 (FIG. 4) to carry high frequency signals to the pacemaker 10. Replacing the micro-coaxial cable of FIG. 4 with two wires, Iout 177 and Vsupply 171, conserves energy by avoiding losses along the cable and precludes breakage of the inflexible cable caused by long-term flexion of the catheter which is common in an implantable system. Vsupply 171, which may be a third coil, is interposed between the outer insulating tube 156 and the exterior silastic sheath 67. To reduce the number of wires within the catheter, thereby reducing the likelihood of wire breakage, Iout 177 is electrically connected to the wire coil conductor 66 which interconnects the pacing ring electrode 68 and the pacemaker 10. It is desirable to limit the number of wires in the catheter to avoid breakage in a chronically implanted device. Since blood flows out of the heart mainly after a ventricular heartbeat, when cardiac electrical information is meaningless and pacing stimulation if prohibited, the device can use a pacing and sensing wire to carry blood flow information.

In a chronically implanted device, it is desirable to conserve power by concentrating transmitted ultrasonic energy on one side of the catheter and orienting the direction of concentration toward the aorta. Referring to FIG. 6, the cylindrical ultrasound transducer 92 is comprised of three cylindrical layers, the outer epoxy window 161, the intermediate cylindrical ultrasound crystals 175 and 176, and the inner epoxy substrate 162, all of which encircle the lumen 155 of lead 13 of FIG. 5. The cylindrical ultrasound transmission crystal 175 lies adjacent to the cylindrical ultrasound receiving crystal 176 within the intermediate cylindrical layer. Each crystal 175 and 176 is electrically connected to probe IC 71 by means of a corresponding circuit which includes two ultrasound electrodes, an interior cylindrical electrode which is attached to the inner surface of each crystal and an exterior cylindrical electrode which is attached to the crystal's outer surface. Ultrasound interior 190 and exterior 191 electrodes electrically connect transmission crystal 175 to probe IC 71 (not shown in FIG. 6) by conductors 190a and 191a, respectively, which correspond to the diagrammatically represented pair of conductors 175a of FIG. 5. Ultrasound interior 192 and exterior 193 electrodes electrically connect receiving crystal 176 to probe IC 71 by conductors 192a and 193a, respectively, which correspond to the diagrammatically represented pair of conductors 176a of FIG. 5. One method for concentrating the transmitted ultrasonic power is to apply ultrasound electrode material (e.g., platinum) to only one side of the ultrasound transducers 175 and 176. In the preferred embodiment of the invention, electrode material coats a semicircular arc of about 60 degrees, extending the length of the long axis of the transmission and receiving crystal cylinders. Exterior electrodes 191 and 193 are separated by etching at the boundary of the transmission and receiving crystals. Interior electrodes 190 and 192 are separated in the same manner. By limiting the placement of electrode material in this manner, the transducer transmits and receives essentially only from the coated side of the catheter 13. During implantation, the device is oriented so that this coated side is directed toward the aorta.

Although embodiments 5A (FIGS. 1 and 2) and 5B (FIGS. 3, 4, 5, and 6) of the cardiac assist or therapy device depict single-chamber pacemakers which sense cardiac signals using leads connected in the bipolar mode, it is to be understood that further embodiments, such as unipolar single-chamber pacemakers, dual-chamber unipolar or bipolar pacemakers, or a cardiac assist or therapy device such as a cardioverter or defibrillator, which does not perform as a pacemaker, are intended to be included within the scope of the invention. For a cardiac assist or therapy device which does not perform pacing, the leads 12 or 13 are replaced by leads which do not include pacing tip electrodes 80 or 91 and ring electrodes 89 or 68 therein. In addition, it is to be understood that the invention can be a pacemaker system which includes pacing leads which are physically separate from an ultrasound catheter or lead.

FIG. 7 illustrates a third example of a cardiac assist or therapy device 5C in the form of a chronically implantable peripheral vascular monitoring controller 24 with a peripheral vascular catheter or lead 26 connecting the controller 24, physically and electrically, to a peripheral cylindrical piezoelectric ultrasound transducer 28. At a location along the length of the catheter 26, the cylindrical piezoelectric transducer 28, which is similar to ultrasound transducer 92 of FIG. 4, is affixed to and surrounds the catheter 26. At this point, the location of which is selected so that the transducer 28 lies within the region of interest for interrogation, the transducer 28 electrically joins with the catheter 26. The catheter 26 extends from the controller 24 into a vein 50 which is in close proximity to an artery 51. The maximum distance between the vein 50 and the artery 51 depends on the range of the piezoelectric transducer 28, and is a function of parameters such as the frequency of the interrogating ultrasound waves and acoustic characteristics of the tissue. The controller 24 electrically excites the ultrasound transducer, causing the piezoelectric elements of the transducer to emit ultrasound waves which extend in all directions perpendicular to the surface of the cylindrical transducer 28. The catheter 26 is implanted in a standard vein for catheterization, as is standard in electrophysiological testing, in a manner such that the cylindrical piezoelectric transducer 28 is located in close proximity and adjacent to the nearby artery 51 so that the artery is characterized by the largest blood volume and highest blood flow velocity within the detection range of the transducer. Implantation requires only standard electrophysiological techniques. Although FIG. 7 illustrates the method of interrogating blood flow within a particular artery from a transducer located within a particular vein, the invention is not so limited and the scope of the invention extends to any accessible vein and nearby artery.

It is to be understood that further variations of the devices 5A–5C illustrated in FIGS. 1 through 5 are intended to be included within the scope of the invention. One example of such a variation is to include multiple ultrasound transducers laterally mounted at various locations along a lead or catheter for measuring cardiac and vascular performance by characterizing the pulsating blood flow profile within discrete segments of a peripheral artery. Another example of such an extension includes an ultrasound transducer implanted within the heart for measuring cardiac output from the aorta in combination with an ultrasound transducer implanted within a peripheral vein to correlate peripheral vascular flow with cardiac output and timing of cardiac events in the heart.

The cardiac assist or therapy devices 5A–5C illustrated in FIGS. 1 through 6 include a means, additional to that utilized for determining cardiac output, for deriving a hemodynamic control parameter, for example ststolic time intervals. The devices may be enabled to measure systolic time intervals, using Doppler ultrasound techniques, by determining blood velocity in the ascending aorta, just above the aortic valve, in the same manner as was performed in the determination of cardiac output, differentiating the resulting blood velocity signal, and finding the minimum differentiated value on the trailing slope of the Doppler waveform signal. The time of this minimum value corresponds to the time of valve closure. The apparatus correlates the timing of these mechanical events with intracardiac electrical events to determine systolic time intervals. One important systolic time interval is the interval from the time of the heart's electrical activation of beating, the R-wave, to the time of value closure.

FIG. 8 comprises one example of a series of graphical representations along a time axis of an intracardiac electrogram 20, a Doppler waveform 21, and a differentiated Doppler signal 22. It shows the correspondence in time between the blood flow as shown by pulsed Doppler signal 21, the velocity of blood flow as displayed by differentiated pulsed Doppler signal 22, and the heart's electrical activity as shown by intracardiac electrogram 20. These waveforms are indicative of the amplitude and timing of signals that would be sensed and measured by the cardiac assist or therapy devices 5A-5C. Measurements of the time intervals between intracardiac electrogram events and electro-mechanical systole events as identified by the Doppler waveform allow the device to measure the systolic time intervals of left ventricular ejection time 35 (LVET) and pre-ejection period 29 (PEP).

The preferred embodiments of the cardiac assist or therapy devices 5A-5C utilize a dual-chamber pacemaker which uses Doppler ultrasound techniques to determine five hemodynamic control parameters: stroke volume, cardiac output, contractility from Doppler waveform slope, myocardial contractility from myofibril motion velocity, and systolic time intervals. These devices derive multiple control parameters to provide for cross-checking which is desirable in a life-support system. They combine one or more of these parameters in a predetermined manner to produce a cardiac performance index (CPI) which defines the hemodynamic status of the patient for usage in the control system. The measurement and determination of multiple control parameters provides a redundancy which enhances the reliability required in an implantable device. Such devices are typically life sustaining mechanisms. The suitability of each of these parameters alone varies depending on the condition of the patient's heart. Some disease processes render a particular parameter unfit for performing control functions. The redundancy of a multiple parameter system is highly desirable because it permits self-checking, elevating the safety of an implanted medical device.

Doppler ultrasound techniques enable the measurement of a signal which yields all of these control parameters with only a small increment in computational burden. Since the computational burden is directly related to energy expenditure, minimizing the number, frequency, and complexity of computations is an important consideration for an implantable device. Such a device may conserve on its energy expenditure by performing ultrasound measurements in a pulsed mode rather than by functioning using continuous wave Doppler techniques. This reduces the duty cycle of the ultrasound transmission. Furthermore, the device performs pulsed Doppler mode sensing in a series of burst operations only at times of interest within the cardiac and the respiratory cycles of the patient to limit the duration of data acquisition and the volume of sampled data.

The devices sense intracardiac electrograms, perform Doppler ultrasound measurements, measure the peak aortic blood flow velocity, determine the slope of the Doppler waveform (the maximum rate of change in blood flow velocity in the aorta in response to a heartbeat), differentiate the peak aortic blood flow velocity waveform with respect to time, and determine the intervals between cardiac electrical and mechanical events. The information contained within these multiple and redundant parameters provide for closed-loop hemodynamic control and self-checking capabilities which are highly desirable in a chronically implanted cardiac assist or therapy medical device.

The dual-chamber pacemaker versions of devices 5A and 5B use the measurement of stroke volume as a hemodynamic control parameter for determining the appropriate pacing mode for responding to the physiological needs of the body at a particular time. Normally, the heart operates efficiently to optimize the stroke volume when the atrium and ventricle are operating in synchrony. In response to stress or exercise the atrium drives the heart to an elevated heart rate, which increases cardiac output and supplies the increased requirements of the body. Such an elevated heart rate is termed a physiological atrial tachycardia. However, in the abnormal case of a pathological atrial tachycardia, the high rate driven by the sinus node of the atrium possibly may not conduct through the atrioventricular node to the ventricle, causing the stroke volume to decrease. The best mode of operation for a dual-chamber pacemaker is to allow the atrium to drive the heart rate, resulting in atrioventricular (A-V) synchrony, when the atrial rate is physiological, but to pace at a rate not determined by the atrium if the atrial rate is pathological. Therefore, when the dual chamber pacemaker version of the present invention detects an increased intrinsic atrial rate but a decreased stroke volume, it responds by pacing only the ventricle at a rate gradually receding from the high intrinsic atrial rate until the intrinsic atrial rate lowers.

The devices 5A-5C perform rate-responsive cardiac pacing by determining a pacing rate based on one or more of the following hemodynamic control parameters: stroke volume, cardiac output, contractility from the Doppler waveform slope, myocardial contractility from myofibril motion detection, and systolic time intervals. At the onset of stress, emotion or exercise, or even in anticipation of these conditions, in a person with a normal heart, the sympathetic nervous system responds by constricting the interiors of central, visceral and peripheral veins, increasing cardiac contractility, and elevating the heart rate. This causes an increase in stroke volume and cardiac output. The sympathetic nervous system acts in the same manner in pacemaker patients, but the heart often does not have the ability to raise the heart rate. In these patients, the hemodynamic control system of the present invention detects the increase in cardiac contractility, either directly or through the detection of an increase in the slope of the stroke volume (and thereby cardiac output). The pacemaker then responds by gradually increasing the pacing rate by a predetermined amount. When cardiac contractility begins to decrease, the pacemaker gradually reduces the pacing rate.

Cardiac output is equal to the multiplication product of the stroke volume (flow from the heart in a single heartbeat) and the heart rate. In human subjects with a normal and healthy cardiovascular system, increases in metabolic demand due to exercise or other forms of stress lead to a response of the cardiovascular system in which cardiac output rises, mainly because the system elevates the heart rate. Stroke volume varies little between low and high levels of exertion in healthy patients.

In patients afflicted with heart block, the heart is unable to increase the heart rate to meet an elevated metabolic demand. In this case, the cardiac stroke volume increases because the ventricular contraction force strengthens, due to a heightened sympathetic nervous system response, which increases contractility of the myocardium and causes constriction of peripheral blood vessels. The latter, in turn, causes increases the venous blood flow returning to the heart. In these abnormal circumstances, cardiac output increases due to an elevated stroke volume rather than a change in heart rate. The pacemaker then raises the heart rate to facilitate the heart's physiological efforts to increase cardiac output.

The stroke volume hemodynamic parameter may be considered a better measure for detecting changes in metabolic demand and initiating a rate response. If the heart is in reasonable condition, constriction of the veins temporarily elevates the venous return blood flow to the heart, increasing the stroke volume even when the heart is unable to increase its natural rate. The pacemakers in the devices 5A-5C of the present invention use the stroke volume measurement to anticipate the need for an increased heart rate. In general, when the Doppler measurement determines an increase in the stroke volume to a predetermined level, the rate-responsive pacemakers will increase heart rate to supply the elevated needs of the body. When the stroke volume decreases by a predetermined amount, the pacemakers gradually return the heart rate to resting levels. In this manner stroke volume controls the heart rate in a feedback loop. This relationship between stroke volume and metabolic demand deteriorates in diseased hearts, however. Therefore, the preferred embodiments of the invention use the stroke volume measurement in conjunction with other parameters to derive a metabolic indicator pacing rate.

The cardiac output parameter may be considered a better indication of how well the needs of the body are satisfied. The pacemakers in the devices of the present invention use the cardiac output parameter to indicate how well the heart is performing in response to, rather than in anticipation of, the metabolic demands of the body. The pacemakers use the cardiac output measurement to determine the heart's optimum rate, the minimum rate at which further rate decrements will cause a decline in the cardiac output. The pacemakers can slowly modulate the heart rate by alternately increasing and decreasing the rate and measuring the cardiac output in response to the modulation. If the cardiac output increases in response to the modulation, the pacemakers gradually increase the rate to a higher mean level and continue to modulate the rate around this level. If this metabolic indicator pacing rate does not change, or decreases in time, the pacemakers gradually reduce the rate and continue to measure the cardiac output. The pacemakers slowly decrease the rate as long as the reduced rate does not diminish the average cardiac output.

The preferred embodiment of the invention employs a metabolic indicator rate derived from stroke volume, contractility and systolic time interval measurements to set the pacing rate. The pacemakers of the devices 5A-5C can be enabled to also derive a metabolic indicator rate which includes the contribution of a metabolic indicator that is independent of the indicator produced using ultrasound techniques (for example, respiratory minute volume from an impedance measurement). This enhances reliability by protecting against either ultrasound or impedance measurement errors.

The pacemakers of devices 5A-5C sense and analyze the signals which are illustrated in FIG. 8 to determine an indication of cardiac contractility. The pacemakers first measure and analyze the Doppler waveform to determine the slope of the rising edge of the Doppler E wave 25. This slope measurement is the best indication of cardiac contractility. The pacemaker uses this indication of contractility in a feedback loop similar to that of stroke volume to anticipate the need for an increased heart rate. An increase in contractility of a predetermined level, sensed as an increase in the slope of the rising edge of the Doppler E wave 25, causes the pacemaker to increase heart rate to supply the elevated needs of the body. When the contractility decreases by a preset amount the device gradually returns the heart rate to resting levels.

The pacemakers of devices 5A-5C also can be programmed to measure time intervals between cardiac electrical and mechanical events to provide a further indication of myocardial contractility. These time intervals allow the derivation of another hemodynamic control parameter to provide for rate determination in rate-responsive pacing. The pacemakers are programmed by using external programmers which communicate with the pacemakers by means of telemetric links, as is standard in the art of cardiac pacing. For the same reason that the sympathetic nervous system increases stroke volume, by enhancing venous return flow as a result of constriction of the veins, it influences the systolic time intervals. Referring to FIG. 8, the measured systolic time interval is the time period between the onset of the QRS-complex 23 and electromechanical systole. This comprises the duration of consecutive intervals of pre-ejection period 29 (PEP) and left ventricular ejection time 35 (LVET). The systolic time interval decreases in duration in response to the elevated physiological demand inherent in circumstances of exercise, emotion or stress. Conversely, the cessation of physiological demand causes the systolic time interval to increase. As the pacemakers measure the systolic time interval, they determine an appropriate pacing rate depending on physiological demand. The pacemakers increase the rate when the interval diminishes below a predetermined threshold amount above the average or resting level. The pacemakers decrease the rate for longer systolic time interval measurements.

In a similar manner, the pacemakers of devices 5A-5C can time the interval (Q-E interval) between the QRS-complex 23 and the Doppler E wave 25, the first Doppler wave following the R wave as shown in FIG. 8. In addition to its influence on the venous system when anticipating or responding to stress or exercise, the sympathetic nervous system increases the contractility of the heart. The Doppler E wave 25 is a measurement correlated to early diastolic filling, which varies in response to cardiac contractility. A shorter Q-E interval reflects an increased cardiac contractility and enhanced physiological needs. The rate-responsive pacemakers (dual-chamber or single-chamber) of the present invention chronically and continually measure Q-E interval and respond to changes in interval duration by varying heart rate in a negative-feedback closed-loop system, raising heart rate for smaller Q-E intervals and lowering heart rate for larger intervals.

Another function performed by the dual-chamber or single-chamber pacemakers in embodiments 5A–5C of the invention is capture detection, which is the determination of whether a pacing stimulus in the atrium or ventricle (or both chambers) successfully causes the heart to beat. A subthreshold pacing stimulus amplitude fails to elicit a cardiac response, resulting in a substantial and easily detectable decrease in stroke volume, and a diminished or absent Doppler waveform. When the pacemaker measures blood flow velocity in the ascending aorta for a predetermined interval after generating a pacing stimulus, and the resulting Doppler waveform has a maximum value during that measurement window which is smaller than a preset threshold value, the stimulus is considered to have failed to capture the heart. The pacemaker must therefore increase the pacing amplitude. It may adjust the pacing pulse duration as well as the amplitude. The standard cardiac pacemaker strength/duration curves, relating pulse duration to amplitude for producing a supra-threshold pacing stimulus, indicate how the pacemaker can adjust the delivered pacing energy to safely pace the heart.

In addition to pacing pulse amplitude, the devices of the present invention may adjust pacing pulse morphology to most efficiently stimulate cardiovascular tissue. The pulse generation circuitry may produce a biphasic or triphasic pacing pulse in which the pulse generation circuitry varies the polarity, amplitude, and duration of the voltages generated for each phase. Pacing pulses generated in this manner may stimulate cardiovascular tissue with a lower energy expenditure or may reduce polarization artifacts in cases where the device is intended to measure evoked potentials. Whigham et al. U.S. Pat. No. 4,821,724, entitled "Pacing Pulse Compensation", which issued on Apr. 18, 1989, discusses a method and application of pacing pulse morphology control, which description is hereby incorporated by reference. This patent also describes electronic circuitry which is capable of performing the intracardiac electrogram sensing for analyzing intrinsic and evoked potential cardiac signals required to realize the present invention. Such circuitry incorporates the use of a controller, which may be a microprocessor, to govern operation of an implantable apparatus for delivering stimulus pulses to cardiac tissue. The controller initializes, activates, inhibits, and responds to at least one timer circuit, as well as circuitry for sensing external events in at least one cardiac channel. A detailed understanding of these operations is well known in the art.

Cardiac arrhythmia detection and automatic control of a therapy for responding to assist the heart upon the detection of a dangerous arrhythmia is another function of the pacemakers. To perform this function, the present devices derive the parameters quantifying blood volume flow and cardiac contractility, using one or more of the aforementioned procedures. A change in contractility is a good indicator of cardiac arrhythmia. While the pacemaker is sampling data and deriving a hemodynamic control parameter for the purpose of detecting changes in contractility, it performs analysis of the Doppler waveform for the purpose of further checking, in a redundant manner, for the presence of an arrhythmia, prior to initiating an arrhythmia reversion routine. The most important control parameter for the detection of arrhythmia is obtained from analysis of the cardiac output measurement.

Referring to FIG. 8, the Doppler A wave 27 follows the E wave 25. The Doppler A wave 27 is indicative of the amount of atrial filling. A missing or reduced amplitude Doppler A wave indicates atrial fibrillation. When the devices 5A–5C have detected and verified the presence of atrial fibrillation, they either control electrical stimulation of the heart or control a drug infusion pump output to restore sinus rhythm in a manner known in the art. The devices of the present invention, if the function is enabled by an external programming device, also measure cardiac output to distinguish hemodynamically stable ventricular tachycardias from unstable such events. The devices monitor the rate of intrinsic (natural) ventricular heartbeats. If the cardiac output is less than some preset threshold level (for example, fifty percent of an average value) and the rate of ventricular activity is greater than a predetermined tachycardia level, the tachycardia is classified as unstable and the devices initiate a known ventricular tachycardia therapy, either electrical or pharmacological in nature. The detection criterion is a simultaneous occurrence of a decreasing cardiac output and a high rate of intrinsic cardiac activity.

FIG. 9 is a high-level, highly symbolic, schematic block diagram illustrating one example of circuitry supporting the functions and methods comprising the illustrative embodiments of this invention. Other circuits which are common in the art of cardiac pacemakers and antitachycardia/defibrillator devices may be used to perform similar timing, sensing and stimulus generating functions. First and second pairs of tip and ring electrode conductors, 110, 112, and 114, 116, respectively, are commonly found in the two bipolar leads employed in a conventional dual chamber cardiac pacemaker. All device logic is under the control of a controller 100 (which may be a microprocessor). The controller operates various switches to control: (1) the enabling or disabling of intrinsic (or natural) cardiac activity sensing in the atrium (ASENSE) and the ventricle (VSENSE) of the heart by means of control signals communicated to a sensing and depolarization controller 115; (2) the generation of stimulating pulses in the atrium (APACE) and the ventricle (VPACE) by means of control signals extending to an output generator block 102; (3) timers 101; (4) intracardiac electrogram sensing in the atrium (AECG) and ventricle (VECG) by means of control signals communicated to an A/D converter 120; (5) Doppler signal sensing by means of control signals sent to a Doppler signal processor 70; and (6) telemetry block 103. The controller 100 reads digital Doppler signals (DOPP) from the Doppler signal processor 70 output register. Generally, the controller 100 times the activation and the inhibition of stimulation pulse delivery, controls the amplitude and form of each stimulating pulse, controls the sensing of natural cardiac signals ASENSE and VSENSE, and samples data to construct AECG, VECG and DOPP waveforms.

To control Doppler signal acquisition, the controller 100 writes control parameters to programmable registers within the Doppler signal processor 70. The Doppler signal processor acquires blood flow information by transmitting signals into interrogated blood and tissue in bursts of pulsed Doppler acoustic waves. Control information from the controller 100 sets the repetition rate of the bursts (between 20 and 90 Hz), the duration of each Doppler output pulse (between 1.6 and 2.4 usec), the RF oscillator repetition rate, and the depth of the sampling field (by adjusting the delay between transmission and received signal sampling). The controller 100 reads data from the Doppler signal processor 70 then sequentially differentiates, integrates, and filters the DOPP signals to construct a Doppler waveform. Peak signals in the Doppler waveform are a manifestation of mechanical events in the cardiac cycle such as the opening and closing of heart valves.

Although the description of the preferred embodiment of the invention expresses the acquisition of Doppler ultrasound waveforms using pulsed Doppler mode, it is within the spirit and scope of the invention to also acquire the waveforms using continuous wave Doppler mode. The pulsed Doppler mode is preferred over continuous wave Doppler mode in a highly compact, implantable system because the pulsed mode allows for a higher-frequency transducer, requiring an inherently smaller crystal for generating the ultrasonic beam. Additionally, in pulsed Doppler mode, a single crystal acts sequentially as both the transmitter and receiver, avoiding the requirement of a second transducer and thereby reducing the size requirement of the implantable device. Most importantly, however, pulsed Doppler mode requires less energy then continuous wave Doppler mode. Such a reduction in energy requirements is highly desirable in a closed-loop pacemaker control system.

Figure 10:
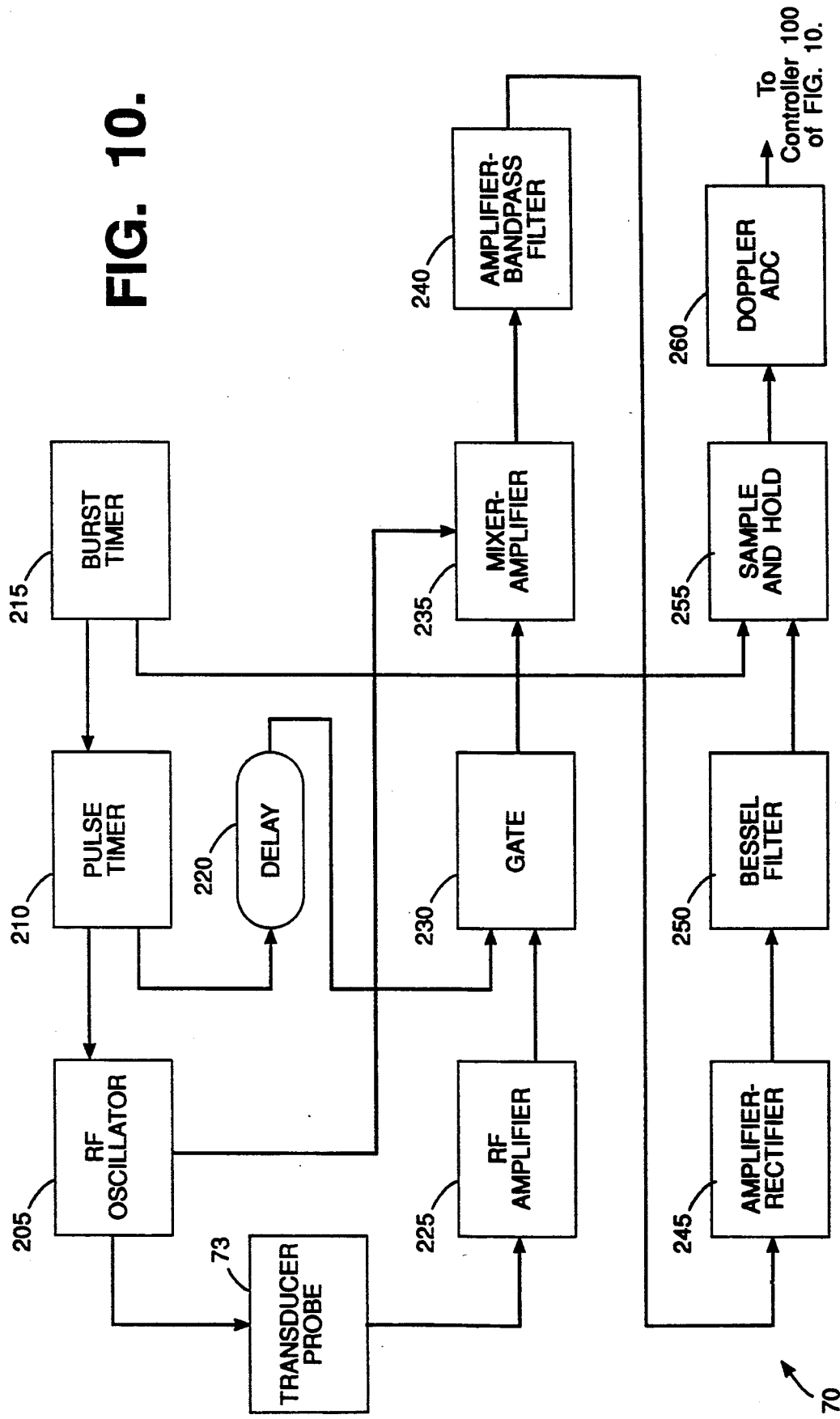
FIG. 10 is a high-level block diagram of a Doppler signal processor circuit that comprises one of the blocks of FIG. 9.

Referring now to FIG. 10, the Doppler signal processor 70 includes a burst timer 215 for producing timing signals at a programmed burst repetition rate ranging in frequency from 20 to 90 Hz. By acquiring pulsed Doppler waveforms in a burst mode, the device further reduces energy expenditure by transmitting acoustic waves only part of the time. The repetition rate must be sufficient to preserve the informational content of the left ventricular output (the pulsatile frequency of which ranges from 1 to 6 Hz) and is controlled by means of control signals from the controller 100 (FIG. 9), which sets the frequency of a Doppler RF oscillator 205. One millisecond duration pulses from the burst timer 215 trigger the activation of a pulse timer 210 which, in turn, produces pulses of a programmable duration (1.6 to 2.4 usec), timing control signals which extend to the RF oscillator 205 and extend to a delay circuit 220. The RF oscillator 205 produces a 7 MHz electrical signal, in the form of a sinusoidal burst of 8 to 12 cycles at a programmable repetition rate of 33 to 100 kHz every 11 to 50 msec, and sends the signal to a Doppler ultrasound transducer or probe 73 (e.g., transducer 86 of FIG. 2, transducer 92 of FIG. 4 or transducer 28 of FIG. 7) via a micro-coaxial cable (e.g. cable 78 of FIG. 2 or cable 163 of FIG. 4). The RF oscillator 205 outputs 2 volts RMS into a 50 ohm load. The RF oscillator also provides a 600 mv RMS electrical signal to a mixer/amplifier 235.

The Doppler ultrasound transducer 73 converts the signal from the RF oscillator 205 into an acoustical waveform which it emits into the body for the purpose of acoustic interrogation. The Doppler ultrasound transducer 73 receives returning echoes from the blood and tissue and converts the returning acoustical waveforms into electrical signals. The receiver connection of the aforesaid micro-coaxial cable passes these signals to an RF amplifier 225. The RF amplifier has a gain of about 1000 to amplify the 0.2 to 20 microvolt signals from the Doppler ultrasound transducer into millivolt level RMS signals which are input into a gate circuit 230. The RF amplifier 225 performs bandpass filtering to produce a waveform with frequency components in the range of from 200 kHz to 8 MHz. The gate circuit 230 performs range gating of the electrical signal processed from the echoes received by the Doppler ultrasound transducer 73. By performing range gating, the Doppler system can measure blood flow information at a particular depth from the transducer rather than detecting information averaged over the entire penetration depth. A control register in the gate circuitry 230, for selecting duration, is programmable in the range of from ten to thirty microseconds to provide for adjustment of the depth of the sampled field. The gate circuit 230 has unity gain and performs bandpass filtering from 100 kHz to 14 MHz.

Timing signals from the delay circuit 220 determine the depth of the ultrasound field of view. The delay circuit 220 performs timing for the purpose of range gating and has a programmable delay of from 15 to 35 usec. The delay circuit 220 and the gate circuit 230 act in concert to determine the measurement range of the Doppler system. The delay circuit sets the distance from the Doppler ultrasound transducer 73 to the start of the field of view at which the system begins sampling. The gate circuit 230 sets the depth ot range of the sampled field of view from the most proximal to the most distal depth of the interrogated blood and tissue. The depth of the actual sampled field of view depend on parameters including the programmed delay and gate values, frequency characteristics of the ultrasound transducer and the speed of sound in the body. When interrogating the ascending aorta from a transducer located in the superior vena cava, the field of view is programmed to a sample depth range of from 3 to 5 cm.

Gated signals from the gate circuit 230 pass to the mixer/amplifier 235 which compares the frequency information of the interrogating and echoed signals to determine velocity within the ultrasound field. The function of determining velocity from acoustic signals as performed by the mixer/amplifier 235 is standard in the art of Doppler measurement devices. An amplifier/bandpass filter 240 is the combination of an audio amplifier (with an audio frequency bandwidth of 370 to 7600 Hz and a gain of 500) and a two pole bandpass filter (with a Q of 1, an adjustable center frequency between 1 and 3 kHz and a midband gain of 2.67). The amplifier/bandpass filter 240 elevates the amplitude of the signal at the mixer/amplifier 235 output from the level of a few millivolts to the range of about one volt. This operation is the first stage in the process of converting the spectral components of the audio signal arising from the mixer/amplifier 235 to a continuously varying voltage.

The output of the amplifier/bandpass filter 240 is an amplitude modulated signal, which is led to an amplifier/rectifier 245. The purpose of amplifier/rectifier 245 is to remove the radio frequency components of the amplitude modulated signal. The first stage of amplifier/rectifier 245 is an amplifier with a fixed gain of 51 and a bandwidth from 10 Hz to 16 kHz. This first stage boosts the signal amplitude and removes high frequency noise resulting from a differentiation operation in the amplifier bandpass filter 240. The final stage of amplifier/rectifier 245 is a full wave, unity gain, precision rectifier with a dynamic range of 30 dB which passes signal frequencies from DC to 10 kHz.

A three pole, unity gain, 6 Hz Bessel filter 250 removes the audio frequency signal components out of the amplitude modulated output of the amplifier/rectifier 245. A sample and hold circuit 255 samples the output of the Bessel filter 250 in preparation for conversion to digital form by a Doppler analog to digital converter (ADC) 260. The digital output of the Doppler ADC 260 is sent to controller 100 of FIG. 9 and is used to determine cardiac output, or to measure pulse wave parameters in the peripheral vascular system, depending on the type of device 5A–5C utilized.

Figure 11:
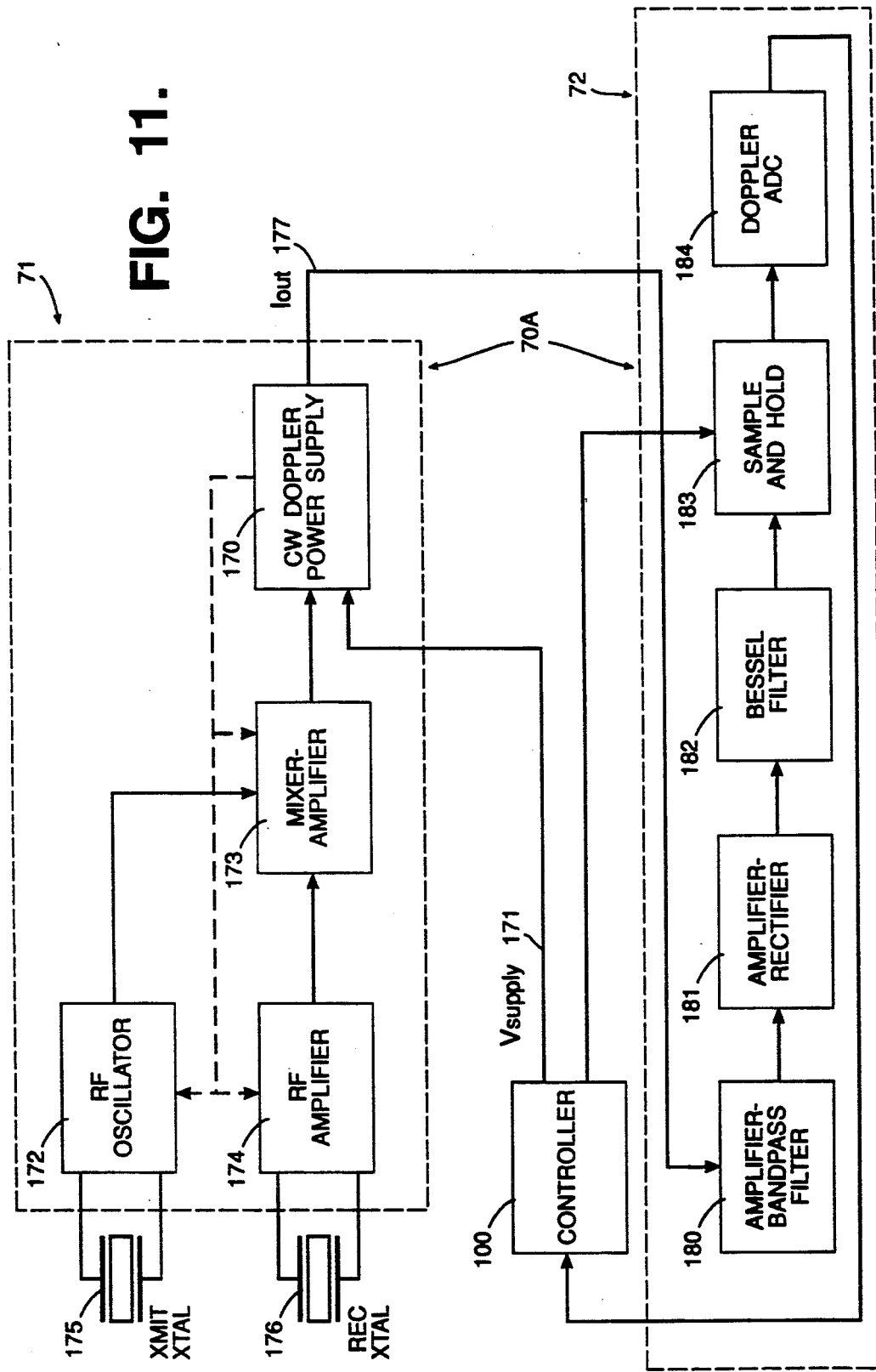
FIG. 11 is a high-level block diagram of a Doppler signal processor circuit that comprises one of the blocks of FIG. 10 in which part of the circuit is located within the lead shown in FIG. 5.

FIG. 11 illustrates a high level block diagram of an additional embodiment of a Doppler signal processor 70A that may be used with the cardiac lead 13 shown in FIG. 5. This processor implements ultrasound measurements in a continuous wave, rather than employing a pulsed mode of operation. A controller 100, which maybe a microprocessor, commands continuous wave Doppler signal processor 70 by controlling delivery of voltage on Vsupply line 171 to CW Doppler power supply 170. Controller 100 performs software routines which determine when to sample blood flow signals. These software routines act as a burst timer to synchronize blood flow sampling with the heart's electrical events. For example, controller 100 detects a QRS-complex within the intracardiac electrogram, waits for a predetermined interval (e.g., 150 ms), then measures blood flow by sampling Doppler signals for another predetermined time (e.g., 100 ms). Controller 100 may measure blood flow on every cardiac cycle, or may sample only occasionally (e.g., every 4 seconds) to conserve energy. This method of operation, in which the transducer interrogates blood flow in timed bursts of ultrasound energy, is called an interrupted continuous wave (CW) Doppler ultrasound technique.

In addition, controller 100 may control the measurement of other physiological parameters which may influence the blood flow measurement. For example, respiration by the patient generates an artifact in the blood flow measurement which may reduce the effectiveness of control methods based on blood flow. A pacemaker may include respiration sensing to control pacing rate, as is disclosed by Nappholz et al. in U.S. Pat. No. 4,901,725, dated Feb. 20, 1990, and entitled "Minute Volume Rate-Responsive Pacemaker". In a system which combines minute ventilation sensing with Doppler ultrasound blood flow measurements, the controller can synchronize the blood flow measurement with respiration (either inspiration or expiration) and with position within the cardiac cycle. In general, the best ultrasound sensing occurs during the expiration portion of the respiratory cycle.

The Doppler signal processor 70A of this embodiment of the invention is comprised of circuits which includes an ultrasound probe integrated circuit (probe IC 71) and an ultrasound signal processor 72. The probe IC 71, which corresponds to probe IC 71 of FIG. 5, is connected to a pair of ceramic crystals 175 and 176 which are mounted near the distal end of a chronic pacing catheter. The probe IC 71 comprises high frequency signal processor circuitry including the CW Doppler power supply 170, an RF oscillator 172, a mixer-amplifier 173, and an RF amplifier 174, all of which are mounted on the catheter within a few millimeters of the ceramic crystals. The ultrasound signal processor 72 is located within the pacemaker case, rather than on the catheter, and communicates with the probe IC electronics by way of two wire coils, Vsupply line 171 and a current output line, Iout 177 (which includes coil 66). The ultrasound signal processor 72 is comprised of an amplifier-bandpass filter 180, an amplifier-rectifier 181, a Bessel filter 182, a sample and hold circuit 183, and a Doppler analog to digital converter (Doppler ADC 184).

When the controller applies voltage on Vsupply line 171, the CW Doppler power supply 170, in turn, provides operating energy to RF oscillator 172, mixer-amplifier 173, and RF amplifier 174. Upon activation, the RF oscillator 172 generates and applies a continuous sinusoidal 8 MHz electrical signal to transmission crystal 175 (e.g., in transducer 92 of FIG. 5). In the preferred embodiment of the invention, the transmission crystal CW power is about 50 uW in 50 ohms. In addition to exciting the transmission crystal, the RF oscillator 172 also provides a 600 mv RMS electrical signal to a mixer-amplifier 173. The transmission crystal 175 acts as a tuning element for RF oscillator 172. This allows tracking between the RF oscillator 172 and the mixer-amplifier 173 oscillator as the transmission crystal 175 absorbs fluids which, in turn, causes a shift in the resonant frequency of the crystal.

The transmission crystal 175 converts a signal from the RF oscillator 172 into an acoustical waveform which it emits into the body for the purpose of acoustic interrogation. The receiver crystal 176 receives returning echoes from the blood and tissue, converts the returning acoustical waveforms into electrical signals, and passes these signals to the RF amplifier 174. The RF amplifier has a gain of about 1000 to amplify the 0.2 to 20 microvolt signals from the Doppler ultrasound transducer into millivolt level RMS signals which are input into the mixer-amplifier 173. The RF amplifier 174 augments the signal from the receiver crystal 176 by a first stage receiver RF gain of at least ten to eliminate voltage noise from subsequent filtering and amplification stages. The mixer-amplifier 173 compares the frequency information of the interrogating and echoed signals to determine velocity within the ultrasound field. The function of determining velocity from acoustic signals as performed by the mixer-amplifier 173 is standard in the art of Doppler measurement devices.

The output signal of the mixer-amplifier 173 is a baseband audio signal which is input to the CW Doppler power supply 170 for the purpose of modulating the power supply load current, Iout 177. Blood flow information is sent from the CW Doppler power supply 170 to the amplifier-bandpass filter 180 circuit using current loop communication in which the baseband audio signal from mixer-amplifier 173 modulates Iout 177. The CW Doppler power supply 170 circuit includes a capacitor which filters the ultrasound frequency signals within the probe IC 71, while retaining and transmitting on Iout 177 the signal variations in the baseband audio load. In this manner, the control commands into the probe IC and output signals representing blood flow are communicated between the pacemaker and the catheter tip by means of two wires, rather than a pair of micro-coaxial cables. In an implantable system, elimination of a coaxial cable is desirable because the cable is subject to the problems of interference between transmit and receive signals, power losses, and breakage from catheter flexure. Coaxial cables commonly have insufficient durability to withstand the large number of flexures common for a pacing catheter. The difficulties are inherent in catheters using wires or coaxial cables to communicate high frequency signals along the catheter length.

Within the ultrasound signal processor 72, the amplifier-bandpass filter 180 is the combination of an audio amplifier (with an audio frequency bandwidth of 370 to 7600 Hz and a gain of 500), a nine pole switched capacitor filter and a two pole bandpass filter (with a Q of 1, an adjustable center frequency between 1 and 3 kHz and a midband gain of 2.67). The amplifier-bandpass filter 180 elevates the amplitude of the signal at the mixer-amplifier 173 output from the level of a few millivolts to the range of about one volt. This operation is the first stage in the process of converting the spectral components of the audio signal arising from the mixer-amplifier 173 to a continuously varying voltage.

The output of the amplifier-bandpass filter 180 is an amplitude modulated signal, which is input to amplifier-rectifier 181. The amplifier-rectifier 181 removes phase variations from the amplitude modulated signal. The first stage of amplifier/rectifier 181 is an amplifier with a fixed gain of 51 and a bandwidth from 10 Hz to 16 kHz. This first stage raises the signal amplitude and removes high frequency noise resulting from a differentiation operation in the amplifier-bandpass filter 180. The final stage of amplifier-rectifier 181 is a full wave, unity gain, precision rectifier with a dynamic range of 30 dB which passes signal frequencies from DC to 10 kHz.

A three pole, unity gain, 6 Hz Bessel filter 182 removes the audio frequency signal components out of the amplitude modulated output of the amplifier-rectifier 181. A sample and hold circuit 183 samples the output of the Bessel filter 182 in preparation for conversion to digital form by a Doppler analog to digital converter (ADC) 184. The digital output of the Doppler ADC 884 is sent to controller 100 and is used to determine cardiac output or to measure pulse wave parameters in the peripheral vascular system.

Figure 12:
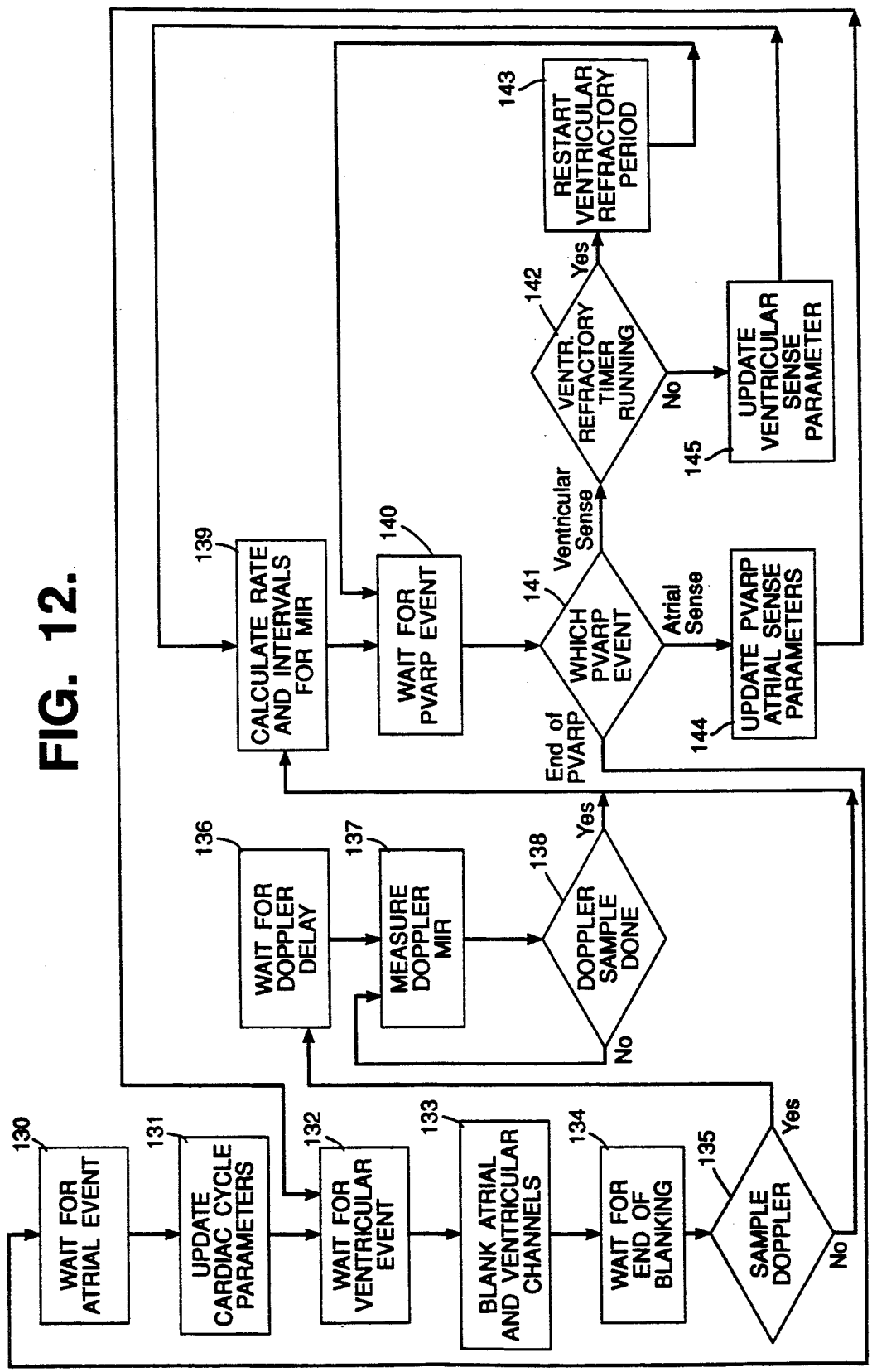
FIG. 12 is a flow diagram illustrating timing, cardiac event detection, and operations performed in the illustrative embodiment of the invention shown in FIG. 9.

FIG. 12 is a flow diagram illustrating the control operations, as time proceeds within a single cardiac cycle, performed by the invention in an embodiment thereof employing a dual-chamber rate-responsive pacemaker. The pacemaker continuously repeats this cardiac cycle. A first block 130 represents the atrial alert wait state in which the pacemaker waits for either ASENSE or the time-out of an atrial timer (one of the timers 101 of FIG. 9). Either of these events defines the end of one cardiac cycle and the beginning of the next. Provided the atrial intrinsic rate is not too high (as determined below), the pacemaker generates an atrial stimulus whenever the atrial timer times out.

Following the atrial event (sense or pace), the pacemaker updates cardiac cycle control parameters. Thus, it enables timers, enables sensing where appropriate in both the atrium and ventricle, analyzes the intrinsic atrial rate to determine whether the intrinsic rate is too fast, and determines the pacing rate from the stroke volume or systolic time interval measurement in an update cardiac cycle parameters block 131. At this time, the device analyzes the atrial intrinsic rate and, as a result of this analysis, controls the pacing mode and determines whether to generate an atrial stimulus. The manner in which the pacemaker controls cardiac cycle parameters depends on whether the event ending the cardiac cycle was ASENSE or atrial timer time-out and for either of these events, whether the pacemaker is operating in an A-V synchronous mode or acting asynchronously in response to atrial tachycardia.

The pacemaker first sets the sinus rate by updating the current P wave to P wave (P-P) interval log to one of two values: (1) the time loaded into the atrial timer at the time of the atrial event in the previous cardiac cycle if the current atrial event is atrial timer time-out, or (2) in the case of ASENSE the time elapsed since the atrial event of the last cycle, the time in (1) reduced by the time remaining in the atrial timer.

Also in the update cardiac cycle parameters block 131, the pacemaker analyzes the intrinsic atrial rate to determine whether it is too fast to permit A-V synchronous pacing. The pacemaker monitors the recent time history of the intrinsic atrial heart rate (the sinus rate) and the metabolic indicator rate (MIR), and a cardiac performance index (CPI) parameter is determined in a rate and interval calculation block 139 for use in evaluating an appropriate pacing mode. The device then sets an atrial tracking rate, a rate distinguishing a high natural physiological rate for responding to exercise or stress from a pathological rate. The pacemaker sets the atrial tracking rate to a value which is a predetermined amount faster than the metabolic indicator rate.

When the sinus rate is slower than the atrial tracking rate, the pacemaker functions in an A-V synchronous mode. In the A-V synchronous mode, the rate of natural atrial heartbeats fixes the timing for ventricular pacing. Thus, with the sinus rate below the metabolic indicator rate (MIR), the pacemaker stimulates the atrium at the MIR and sets the timing to stimulate the ventricle after an A-V delay. When the sinus rate of the heart rises above the atrial tracking rate and, simultaneously, the pacemaker detects a decreasing cardiac performance index, it classifies the heart rate as a pathological rhythm. The pacemaker responds by pacing the ventricle alone at the metabolic indicator rate in a non-synchronous pacing mode. The pacemaker continues to pace synchronously even at sinus rates above the atrial tracking rate if the heart maintains the cardiac performance index CPI within predetermined limits. Even in the non-synchronous mode, the pacemaker continues to monitor the sinus rate but only for the purpose of determining when to re-establish synchronous pacing. When the intrinsic sinus rate falls below the atrial tracking rate or the cardiac performance index begins to increase consistently, the pacemaker will return to pacing in the A-V synchronous mode.

The pacemaker times the next cycle length (A-A interval) by initializing the atrial timer to the interval specified by the MIR. This interval, in milliseconds, is 60,000 divided by the MIR (in beats per minute). Generally, the pacemaker immediately sets the A-A interval timer to the interval set by the MIR. However, in circumstances when either the sinus rate or the MIR vary rapidly, the pacemaker may change the pacing rate more gradually to provide for a smoother rate response.

If the pacemaker is performing in the A-V synchronous mode, it generates a stimulating pulse (APACE). After atrial timer time-out, the pacemaker divides the A-V delay interval into two subintervals timed by a subinterval timer. In the first, a blanking interval typically of 80 milliseconds duration, the pacemaker disables ASENSE and VSENSE for long enough to prevent sensing of the atrial pacing pulse, its artifact, and any evoked potential. After the first subinterval timer time-out, the pacemaker resets the subinterval timer to an interval of typically 70 milliseconds which, when added to the first blanking interval, comprises the A-V delay interval. The pacemaker enables VSENSE at this time to allow intrinsic ventricular R waves to inhibit VPACE. If the event ending the cardiac cycle was ASENSE and the pacemaker is operating in the DDDR mode, it sets the A-V delay interval timer. The A-V delay value is based on the time between APACE and VSENSE for normal atrioventricular conduction for the patient. The pacemaker modifies the A-V delay by a latency factor, as is known in the art, to account for differences in conduction time between paced atrial activity (APACE) and intrinsic atrial activity (ASENSE). The value of the latency factor may vary depending on such conditions as location of the leads, atrial sense threshold, and atrial sensitivity. At the subsequent A-V delay time-out, the pacemaker will stimulate the ventricle (VPACE), unless pacing is inhibited by VSENSE. During the A-V delay interval, the pacemaker disables ASENSE.

A block 132 represents the ventricular alert wait state in which the pacemaker waits for either VSENSE or the time-out of the A-V delay interval. Upon either event, in a blanking control operation of block 133, the pacemaker disables ASENSE and VSENSE and times a blanking interval corresponding to the atrial absolute refractory period (AARP). Because within the AARP natural P waves are not physiologically possible, the pacemaker blanks (disables sensing) to avoid atrial sensing of extraneous events such as ventricular stimulation, stimulus artifact, and evoked potential. If the ventricular event ending the ventricular alert wait state was the time-out of the A-V delay timer rather than VSENSE, then the pacemaker generates a stimulating pulse (VPACE).

The pacemaker waits for the end of blanking in block 134. Blanking is short enough to allow sampling of the entire Doppler waveform.

The pacemaker establishes whether to sample the Doppler waveform in a block 135. If the sinus rate is below a particular threshold value but above the minimum rate, which is set to the metabolic indicator rate increased or decreased by a predetermined offset value, the pacemaker may sample the Doppler waveform less frequently than every cardiac cycle to reduce energy expenditure. If the pacemaker is to measure the Doppler signal in the current cycle, it begins timing a delay interval between VPACE and the start of Doppler measurement sampling. Systolic time intervals are normally measured from the time of the Q wave event to the time of events identified on the Doppler waveform. The information available to the pacemaker is the time of VSENSE or VPACE. This time is more closely correlated with R wave than Q wave timing. The pacemaker estimates the time of the Q wave event from the known information (VSENSE and VPACE) and stores this estimate in a memory location (QSTART). Now the pacemaker controller 100 of FIG. 9 writes control information to the Doppler signal processor 70, including data codes for specifying the burst repetition rate, the Doppler pulse duration, the field of view, and filtering characteristics.

In a Doppler measurement block 137, the pacemaker performs Doppler ultrasound data acquisition for the purpose of calculating stroke volume and systolic time intervals. The pacemaker waits a predetermined delay in Doppler delay block 136, then begins ultrasound sampling in block 137 and continues sampling for a preset number of samples programmed into a Doppler sampling completed block 138, the pacemaker controller samples the Doppler signal at regular intervals (for example, 8 msec), by writing a sample command to the Doppler signal processor and reading the result (DOPP) when the measurement is available. The pacemaker controller temporarily saves each DOPP sample reading in a time sample array memory. The controller performs filtering operations on the time domain signal, including low pass filtering to reduce signal noise. The pacemaker samples DOPP, stores the time domain signal in memory and differentiates the time domain signal for a number of samples. The number of samples is preset by an external programmer and is related to the duration of the features of interest in the Doppler waveform. After acquiring the final sample, the pacemaker performs analysis to extract features from the Doppler waveform, the filtered waveform, and its derivative. The extracted features include parameters such as the peak signal value, the slope of the rising edge of the Doppler E wave, the integral of the Doppler waveform, the pre-ejection period (PEP) interval, and the left ventricular ejection time (LVET). The peak signal value determines stroke volume.

In block 139, the pacemaker derives the metabolic indicator rate MIR from a combination of hemodynamic control parameters measured using Doppler ultrasound techniques. These hemodynamic control parameters include the stroke volume, the cardiac output, the cardiac contractility from Doppler waveform slope and myocardial motion measurements, and systolic time interval parameters measured using Doppler ultrasound. The pacemaker first analyzes the integral of the maximum blood flow velocity in the aorta. The pacemaker accumulates this integral in the Doppler measurement block 137 for the purpose of determining the relative stroke volume and cardiac output indicators. Because the Doppler ultrasound measurement produces a relative rather than an absolute quantity for both stroke volume and cardiac output, the pacemaker averages these figures over time. When the pacemaker determines that the stroke volume is increasing over the average value, it increases the stroke volume component of the MIR. When the stroke volume is below the average value, the pacemaker lessens the MIR component. The amount of change in the MIR component depends on the magnitude of change in the stroke volume measurement. The pacemaker performs lowpass filtering to average the stroke volume measurement, thereby lessening the influence of noise on the MIR.

Performing in the manner of the stroke volume measurement, the pacemaker determines the contractility component of the MIR. Contractility is proportional to the slope of the rising edge of the Doppler E wave, which value was acquired in block 137. The pacemaker also measures myocardial motion, by means of an additional Doppler ultrasound transducer which is implanted in the septum between the left and right chambers of the heart, to provide an additional indication of contractility from the left ventricle. If the contractility increases by a predetermined amount as compared to its average value, the pacemaker raises the MIR a programmed increment the size of which depends on the size of the contribution attributed to the contractility component. Likewise, if the contractility decreases by a predetermined amount in comparison to the average contractility value, the pacemaker decreases the MIR. In this manner, the procedure for changing MIR in response to changes in contractility includes a dead zone in which variations from the average rate of less than a particular value do not cause the MIR to change. The pacemaker changes MIR in response to variations in the systolic time interval (STI) parameter in a manner similar to the method for changing MIR based on the stroke volume measurement, except that the trends of the two parameters are inversely correlated; i.e., a decreasing stroke volume correlates with a lengthened systolic time interval.

The pacemaker assigns a predetermined weight to each of the MIR parameters and determines the overall metabolic indicator rate from the sum of the MIR components. If the combined MIR is stable or decreasing over a number of cardiac cycles, the pacemaker performs rate modulation to determine the best pacing rate by gradually reducing the rate so long as the cardiac output does not decrease.

Also in block 139, the pacemaker determines the cardiac performance index CPI from a weighted combination of the contractility measures of stroke volume, Doppler waveform slope, and myocardial motion parameters. The recent time history of each of these contractility parameters varies proportionally with the cardiac performance index. When the relative magnitudes of the stroke volume, the slope of the Doppler E waveform, and the myocardial motion increase in time, the cardiac performance index increases. When each of the parameters has a diminishing trend, the cardiac performance index decreases. The pacemaker analyzes the recent history of each of these parameters to determine whether each is increasing, decreasing or remaining constant. A positive or negative value is assigned to the trend for each parameter. The cardiac performance index is the sum of the trend values for each parameter.

It is in block 139 that the pacemaker uses the MIR to calculate the new A-V delay and post-ventricular atrial refractory period (PVARP) values, as well as the new cycle length (A-A interval). PVARP timing begins at this time. The pacemaker senses atrial activity during PVARP for the purpose of detecting atrial tachycardias. In the final operation within the rate and interval calculation block 139, the pacemaker prepares for atrial and ventricular refractory operations. In the atrium, the pacemaker enables ASENSE for sensing during the newly set PVARP interval. The pacemaker delays enabling ventricular sensing until the end of the ventricular blanking period (about 70 milliseconds beyond the 80 msec atrial blanking period) because VSENSE during the ventricular absolute refractory period is not a significant event with regard to cardiac physiology (any sensed signal must be noise).

The pacemaker now waits for ASENSE, VSENSE and PVARP timer events in a wait for PVARP event block 140. Logic blocks 141 and 142 guide the flow of control, dependent upon the detection of one of the three events. Time-out of the PVARP timer ends the PVARP, after which block 141 controls a branch to wait for atrial event block 130. The atrial alert period always follows a PVARP time-out.

If the PVARP event is a ventricular sense (VSENSE), then in block 142 the pacemaker performs a test to determine whether a ventricular refractory timer is running. As described above, initially the pacemaker times a 70 millisecond absolute refractory interval. The pacemaker ignores all ventricular sense events which occur during this interval. After this absolute refractory interval, the pacemaker times a 150-millisecond relative refractory interval. An R wave sensed during the relative refractory interval restarts the 150 msec timer but otherwise has no effect on the operation of the pacemaker (the R wave is treated as noise and is ignored). The pacemaker's flow of control proceeds to block 143 within the first 70 millisecond absolute refractory interval of the ventricular refractory timer. Thus, the pacemaker ignores the foregoing ventricular R-wave sensed during the relative refractory interval and returns to block 140 where the system again waits for a PVARP event. If the pacemaker enters block 143 before time-out of the ventricular refractory timer (i.e., within 220 milliseconds after the beginning of the PVARP interval), the pacemaker restarts the timer and the system notes that relative refractory timing is in progress. Subsequent entries into block 143 do the same thing; in every case the pacemaker returns control to block 140. If a ventricular sense event occurs when the timer has proceeded beyond 150 milliseconds in a relative refractory interval, it is an indication that a premature ventricular contraction has occurred, i.e., a ventricular beat during the PVARP but after the ventricular absolute and relative refractory periods.

The pacemaker responds to such a premature ventricular contraction sensing event in an update ventricular sense parameters block 145 and then branches to the calculate rate and intervals from MIR block 139. Atrial events should always precede ventricular events. Occurrence of a premature ventricular event, one anticipating the atrial event for that cardiac cycle, signifies the end of the cardiac cycle. Because a ventricular event has just occurred, the pacemaker advances to the next cardiac cycle by disabling ASENSE and VSENSE in block 145 and branching to block 139. One modification to the usual processing is now required. There is a timer running which times the A-A interval. This timer requires a new value. Instead of timing a full cycle from the last P wave or APACE, the pacemaker needs to time the V-A interval from the R wave which was just sensed. The pacemaker subtracts the A-V delay from the total A-A cycle length (the time loaded into the A-A timer in block 131), and uses the resulting V-A interval to set the timer defining the time-out event ending block 130.

In an update PVARP atrial sense parameters block 144, the pacemaker responds to ASENSE events falling within the PVARP interval. First the pacemaker measures the immediate P wave to P wave (P-P) interval by reducing the time interval last loaded into the atrial timer by the time left in the atrial timer. The current instantaneous atrial timer value holds the time left in the atrial cycle if the timer, like all timers in the preferred embodiment of the invention, is a down counter. The pacemaker uses the latest P-P interval value to update the running P-P interval average. In addition, the pacemaker sets the A-A interval timer, the A-V delay, and the blanking interval in the manner discussed in the description of the operations of block 131.

It will be apparent from the foregoing description that the present invention makes it possible to quantify a parameter representing the hemodynamic status of a patient's heart. This quantification is achieved by employing a sensor, which is located outside the left heart, to measure systolic time intervals. On the basis of this parameter, the present invention controls the administration of a therapy, either electrical or pharmaceutical, which regulates this hemodynamic status.

Although the invention has been described with reference to particular embodiments, it is to be understood that these embodiments are merely illustrative of the application of the principles of the invention. Numerous modifications may be made therein and other arrangements may be devised without departing from the true spirit and scope of the invention, as set forth in the appended claims.

We claim:

1. A hemodynamic control apparatus for determining a patient's hemodynamic status and adjusting the hemodynamic output of the patient's heart to correspond to the patient's metabolic needs, comprising:

means for generating electrical stimulation pulses and delivering said pulses to the patient's heart, means for sensing natural and pulse-stimulated cardiac electrical signal events of the patient's heart, ultrasonic means implanted within the patient's cardiovascular system for monitoring the volume of blood flowing per unit of time within the cardiovascular system, means for detecting cardiovascular mechanical events from the monitored change in the blood flow volume per unit of time, means for timing intervals between said cardiovascular mechanical events and at least one of said generated stimulation pulses, said sensed natural electrical signal events, and said sensed pulse-stimulated electrical signal events, means for determining a cardiac performance index based on said timed intervals, and means for adjusting said pulse generating means as a function of said cardiac performance index.

2. A hemodynamic control apparatus in accordance with claim 1, wherein said means for adjusting said pulse generating means adjusts at least one of the pulse generation parameters from the group of pulse generation parameters comprising electrical stimulation pulse timing, electrical stimulation pulse duration, electrical stimulation pulse amplitude, electrical stimulation pulse polarity, pacing mode and pacing rate.

3. A hemodynamic control apparatus in accordance with claim 2, wherein said ultrasonic means includes ultrasonic transmitting means utilizing timed bursts of ultrasonic pulses, and ultrasonic receiving means for monitoring said timed intervals.

4. A hemodynamic control apparatus in accordance with claim 3, wherein said ultrasonic means is adapted to be implanted within the patient's right heart for ensonifying the patient's ascending aorta with ultrasonic energy and detecting returning ultrasonic energy reflected from blood cells within the ascending aorta.

5. A hemodynamic control apparatus in accordance with claim 3, wherein said ultrasonic means is adapted to be implanted within the patient's right heart for ensonifying the patient's subclavian artery with ultrasonic energy and detecting returning ultrasonic energy reflected from blood cells within the subclavian artery.

6. A hemodynamic control apparatus in accordance with claim 3, wherein said ultrasonic means includes at least one catheter-mounted ultrasonic sensor, and wherein said ultrasonic sensor is adapted to be implanted within the patient's cardiovascular system in a vein for ensonifying an artery adjacent to the vein with ultrasonic energy and detecting returning ultrasonic energy reflected from blood cells within the adjacent artery.

7. A hemodynamic control apparatus in accordance with claim 1, wherein said generating means includes means for generating ventricular pacing pulses, wherein said natural cardiac signal sensing means includes means for sensing atrial heart beats, and wherein said apparatus further comprises:

means for determining a metabolic indicator rate as a function of said cardiac performance index and independent of the rate of sensed natural atrial heart beats, means for classifying whether the sensed natural atrial heart rate is physiological or pathological based on the sensed natural atrial heart rate, the metabolic indicator rate and the cardiac performance index, and control means operative when the sensed natural atrial heart rate is physiological for keying the operation of said ventricular pacing pulse generating means to the operation of said atrial heart beat sensing means, and operative otherwise for keying the operation of said ventricular pacing pulse generating means to said metabolic indicator rate.

8. A hemodynamic control apparatus in accordance with claim 7, wherein said cardiac performance index determining means and said metabolic indicator rate determining means further include:

means responsive to said ultrasonic blood flow volume monitoring means for sampling and storing a Doppler ultrasound time waveform, and means for analyzing changes in the morphology of the Doppler ultrasound time waveform to determine myocardial contractility.

9. A hemodynamic control apparatus in accordance with claim 8, wherein said classifying means defines an atrial tracking rate which is proportional to said metabolic indicator rate, and wherein said classifying means classifies the sinus heart rate as pathological when the sensed natural atrial heart rate is faster than said atrial tracking rate and the cardiac performance index is decreasing.

10. A hemodynamic control apparatus in accordance with claim 9, wherein said means for adjusting said pulse generating means adjusts at least one of the pulse generation parameters from the group of pulse generation parameters comprising electrical stimulation pulse timing, electrical stimulation pulse duration, electrical stimulation pulse amplitude, electrical stimulation pulse polarity, pacing mode and pacing rate.

11. A hemodynamic control apparatus in accordance with claim 10, wherein said ultrasonic means includes ultrasonic transmitting means utilizing timed bursts of ultrasonic pulses, and ultrasonic receiving means for monitoring said timed intervals.

12. A hemodynamic control apparatus in accordance with claim 9, further including:

means for determining a cardiac performance index minimum value characterizing the threshold level of hemodynamic output resulting from generated ventricular pacing pulses which successfully stimulate the heart, means for comparing subsequent cardiac performance indices resulting from ventricular pacing pulses to said cardiac performance index minimum value, and control means responsive to said comparing means for adjusting the energy level of said generated ventricular pacing pulses to safely stimulate the heart so that the cardiac performance indices will consistently exceed the cardiac performance index minimal value.

13. A hemodynamic control apparatus in accordance with claim 9, wherein said ultrasonic means is adapted to be implanted within the patient's right heart for ensonifying the patient's ascending aorta with ultrasonic energy and detecting returning ultrasonic energy reflected from blood cells within the ascending aorta.

14. A hemodynamic control apparatus in accordance with claim 9, wherein said ultrasonic means is adapted to be implanted within the patient's right heart for ensonifying the patient's subclavian artery with ultrasonic energy and detecting returning ultrasonic energy reflected from blood cells within the subclavian artery.

15. A method of operating a hemodynamic control apparatus for determining a patient's hemodynamic status and adjusting the hemodynamic output of the patient's heart to correspond to the patient's metabolic needs, comprising the steps of:
    generating electrical stimulation pulses and delivering said pulses to the patient's heart,
    sensing natural and pulse-stimulated cardiac electrical signal events,
    ultrasonically monitoring the volume of blood flowing per unit of time within the patient's cardiovascular system,
    detecting cardiovascular mechanical events from the monitored change in the blood flow volume per unit of time,
    timing intervals between said cardiovascular mechanical events and at least one of said generated stimulation pulses, said sensed natural electrical signal events, and said sensed pulse-stimulated electrical signal events,
    determining a cardiac performance index based on said timed intervals, and adjusting said electrical stimulation pulses based on said cardiac performance index.

16. A method of operating a hemodynamic control apparatus in accordance with claim 15, wherein said adjusting step adjusts at least one of the pulse generation parameters from the group of pulse generation parameters comprising electrical stimulation pulse timing, electrical stimulation pulse duration, electrical stimulation pulse amplitude, electrical stimulation pulse polarity, pacing mode and pacing rate.

17. A method of operating a hemodynamic control apparatus in accordance with claim 15, wherein said step of ultrasonically monitoring the volume of blood flowing per unit of time within the patient's cardiovascular system includes the steps of ensonifying the ascending aorta with ultrasonic energy and detecting the returning ultrasonic energy reflected from blood cells within the ascending aorta.

18. A method of operating a hemodynamic control apparatus in accordance with claim 15, wherein said generating step includes the step of generating ventricular pacing pulses, wherein said natural cardiac signal sensing step includes the steps of sensing atrial heart beats, and wherein said method further comprises the steps of:
    determining a metabolic indicator rate as a function of said cardiac performance index and independent of the rate of sensed natural atrial heart beats,
    classifying the sensed natural atrial heart rate as either physiological or pathological based on the sensed natural atrial heart rate, the metabolic indicator rate and the cardiac performance index, and
    keying the operation of said ventricular pacing pulse generating step to the operation of said atrial heart beat sensing step when the sensed natural atrial heart rate is physiological and keying the operation of said ventricular pacing pulse generating step to said metabolic indicator rate otherwise.

19. A method of operating a hemodynamic control apparatus in accordance with claim 18, wherein said steps of determining cardiac performance index and determining a metabolic indicator rate further comprise the steps of:
    sampling and storing data from said ultrasonically monitoring step in the form of a Doppler ultrasound time waveform, and
    analyzing changes in morphology of the Doppler ultrasound time waveform to determine myocardial contractility.

* * * * *